(12) United States Patent
Rigatti et al.

(10) Patent No.: US 10,370,709 B2
(45) Date of Patent: *Aug. 6, 2019

(54) COMPOSITIONS AND METHODS FOR SEQUENCING NUCLEIC ACIDS

(71) Applicant: Ilumina Cambridge Limited, Essex (GB)

(72) Inventors: Roberto Rigatti, Arco (IT); Jonathan Mark Boutell, Essex (GB); Jason Betley, Essex (GB); Niall Anthony Gormley, Essex (GB)

(73) Assignee: Illumina Cambridge Limited, Essex (GB)

( * ) Notice: Subject to any disclaimer, the term of this patent is extended or adjusted under 35 U.S.C. 154(b) by 70 days.

This patent is subject to a terminal disclaimer.

(21) Appl. No.: 15/263,203

(22) Filed: Sep. 12, 2016

(65) Prior Publication Data

US 2016/0376649 A1    Dec. 29, 2016

Related U.S. Application Data

(63) Continuation of application No. 14/299,254, filed on Jun. 9, 2014, now Pat. No. 9,441,272, which is a continuation of application No. 13/825,956, filed as application No. PCT/US2011/053763 on Sep. 28, 2011, now Pat. No. 8,759,038.

(60) Provisional application No. 61/387,900, filed on Sep. 29, 2010.

(51) Int. Cl.
  *C12Q 1/68* (2018.01)
  *C12P 19/34* (2006.01)
  *C12Q 1/6874* (2018.01)
  *C12Q 1/6806* (2018.01)

(52) U.S. Cl.
  CPC ......... *C12Q 1/6874* (2013.01); *C12Q 1/6806* (2013.01); *C12Q 2525/101* (2013.01); *C12Q 2525/186* (2013.01); *C12Q 2525/191* (2013.01)

(58) Field of Classification Search
  CPC ........... C12Q 1/6874; C12Q 2525/101; C12Q 2525/186; C12Q 2525/191; C12Q 2535/122; C12Q 2565/537; C12Q 2565/543; C12Q 1/6806; C12Q 2521/319; C12Q 2523/301
  USPC .................................................. 435/91.2, 6.1
  See application file for complete search history.

(56) References Cited

U.S. PATENT DOCUMENTS

| | | | |
|---|---|---|---|
| 5,654,413 A | 8/1997 | Brenner | |
| 8,753,816 B2 * | 6/2014 | Rigatti | C12Q 1/6874 435/6.1 |
| 8,759,038 B2 * | 6/2014 | Rigatti | C12Q 1/6806 435/91.2 |
| 9,441,272 B2 * | 9/2016 | Rigatti | C12Q 1/6806 |
| 2009/0088327 A1 * | 4/2009 | Rigatti | C12Q 1/6874 506/4 |
| 2010/0111768 A1 * | 5/2010 | Banerjee | C12Q 1/6869 422/82.08 |

FOREIGN PATENT DOCUMENTS

| | | |
|---|---|---|
| EP | 2233582 | 9/2010 |
| WO | 2009120374 | 10/2009 |
| WO | 2010059731 | 5/2010 |

OTHER PUBLICATIONS

Hernandez et al., "De novo bacterial genome sequencing: millions of very short reads assembled on a desktop computer", Genome Research, vol. 18, No. 5, 2008, 802-809.

Ramanathan et al., "An integrative approach for the optical sequencing of single DNA molecules", Analytical Biochemistry, vol. 330, No. 2, 2004, 227-241.

Shendure et al., "Accurate Multiplex Polony Sequencing of an Evolved Bacterial Genome", Science, vol. 309, Sep. 9, 2005, 1728-1732.

* cited by examiner

*Primary Examiner* — Cynthia B Wilder
(74) *Attorney, Agent, or Firm* — Illumina, Inc.

(57) ABSTRACT

Disclosed herein are compositions and methods for sequencing nucleic acids.

13 Claims, 7 Drawing Sheets

Figure 3: Preamplification prior to making deletions (different adaptors)

COMPOSITIONS AND METHODS FOR SEQUENCING NUCLEIC ACIDS

CROSS-REFERENCE TO RELATED APPLICATIONS

This application is a continuation of U.S. application Ser. No. 14/299,254, filed Jun. 9, 2014, now U.S. Pat. No. 9,441,272, which is a continuation of U.S. application Ser. No. 13/825,956, filed Jun. 10, 2013, now U.S. Pat. No. 8,759,038, which is a national stage under 35 U.S.C. § 371 of International Application No. PCT/US2011/053763, filed Sep. 28, 2011, which claims the benefit under 35 U.S.C. § 119(e) of U.S. Provisional Application No. 61/387,900, filed Sep. 29, 2010, the entirety of each of which is hereby incorporated by reference.

FIELD OF THE INVENTION

The present invention relates to the fields of biochemistry and molecular biology. More specifically, the present invention relates to methods and compositions for sequencing nucleic acids.

BACKGROUND

Nucleotide sequencing has become an important technology in medicine and the life sciences. Recently, nucleotide sequencing platforms have become available and reduced the cost of nucleotide sequencing. However, current sequencing technology is limited in terms of the turnaround time for obtaining sequence information and read length of the nucleic acid being sequenced. Thus, there is a need for developing sequencing technology that reduces the time to obtain sequence data and allows for sequencing of longer template samples.

SUMMARY OF THE INVENTION

Embodiments of the present invention relate to methods for sequencing nucleic acids. Some aspects of such methods relate to generating overlapping sequencing reads by processing a plurality of polynucleotides so as to produce a set of overlapping nucleotide regions to be sequenced, providing a substrate having a surface which comprises a site having the set of overlapping nucleotide regions attached thereto, and sequencing the set of overlapping nucleotide regions, thereby generating a set of overlapping sequencing reads.

In some aspects, the method further includes assembling sequencing reads from the set of overlapping sequencing reads to obtain a contiguous nucleotide sequence of a nucleic acid of interest. In some embodiments of the methods, at least one of the polynucleotides includes the contiguous nucleotide sequence of the nucleic acid of interest.

In some aspects of the sequencing methods described herein, processing the plurality of polynucleotides to produce a set of overlapping nucleotide regions to be sequenced includes generating an overlapping set of deletion products from the plurality of polynucleotides. In several aspects, the plurality of nucleotides is attached to the site on the surface of the substrate before the processing step. In other aspects, the plurality of nucleotides is attached to the site on the surface of the substrate after the processing step. In some embodiments, the method further includes amplifying the set of deletion products on the surface to form amplicons corresponding to the set of deletion products. With respect to other aspects of sequencing methods described herein, the processing step includes copying the polynucleotides to produce a plurality of polynucleotide copies, wherein the polynucleotide copies include a modified nucleotide that indicates the beginning of each nucleotide region to be sequenced.

Certain embodiments of the methods described herein relate to nucleic acid sequencing methods that include the steps of providing a substrate having a surface that includes a site having a plurality of polynucleotides attached thereto, generating deletion products from the plurality of polynucleotides, amplifying the deletion products on the surface to form amplicons corresponding to the deletion products, and obtaining nucleotide sequence information from nucleic acids present in the amplicons.

In some such embodiments, the deletion products include overlapping deletion products. In certain of these embodiments, the method further includes assembling nucleotide sequence information corresponding to the overlapping deletion products, thereby producing a contiguous nucleotide sequence of a nucleic acid of interest.

In some embodiments of the sequencing methods described herein, providing the substrate includes hybridizing a plurality of template nucleic acids to a plurality of primers attached to the site. In some such embodiments, each template nucleic acid includes an adaptor that is complementary to a primer sequence. In other such embodiments, the plurality of primers includes first primers and second primers, wherein the first primers and the second primers include a different nucleotide sequence. In still other embodiments, the methods further include extending the primers, thereby producing extended strands. Additionally some of the methods described herein further include pre-amplifying the extended strands prior to generating deletion products. In yet other embodiments of the methods described herein, generating deletion products includes extending the primers in the presence of one or more terminator nucleotides such that the primers are extended to lengths that are less than the full length of the template nucleic acid. In still other embodiments, the method includes dehybridizing the template nucleic acids, thereby producing single-stranded deletion products. Moreover in some embodiments, the method includes attaching an adaptor to a free end of the single-stranded deletion products. In still other embodiments, generating deletion products includes extending the primers in the presence of uracil such that the primers are extended to lengths that are less than the full length of the template nucleic acid.

In some aspects of the sequencing methods described herein, generating deletion products includes digesting the plurality of polynucleotides with an exonuclease. In other aspects, generating deletion products includes physically shearing the polynucleotides. In some such aspects, the polynucleotides include double-stranded polynucleotides having a nick, and generating deletion products includes translating the nick less than the full length of the polynucleotides and cleaving at the nick.

In some of the nucleic acid sequencing methods described herein, the deletion products include an oligonucleotide tag. In some such embodiments, the oligonucleotide tag is complementary to a sequencing primer.

Additional embodiments of the sequencing methods described herein relate to provision of a substrate having a surface. In some embodiments, the substrate includes a flow chamber. In some embodiments, the surface of the substrate is planer. In other embodiments, the surface of the substrate is patterned. In still other embodiments, the surface includes a channel in a flow chamber.

Further embodiments of the sequencing methods described herein relate to provision of a substrate having a surface comprising sites. In some embodiments, a site can include a well. In some embodiments, sites can include a bead in a well.

Certain of the nucleic acid sequencing methods set forth herein comprise the steps of providing a substrate having a surface including a site having a plurality of primers attached thereto, contacting the plurality of primers with a plurality of template nucleic acids, extending the primers in the presence of a first modified nucleotide such that the first modified nucleotide is incorporated in a plurality of extended strands, synthesizing a complement of the extended strands using a polymerase that incorporates a second modified nucleotide complementary to the first modified nucleotide, and initiating a sequencing read from the point of incorporation of the first modified nucleotide, thereby producing nucleic acid sequence information.

In some aspects, the methods include initiating a sequencing read from the point of incorporation of the second modified nucleotide. In some aspects, the methods include amplifying the extended strand and the complement to form amplicons prior to initiating the sequencing read.

In additional aspects of the sequencing methods described above, the sequence information includes a set of overlapping sequencing reads. In some such aspects, the method includes the step of assembling overlapping sequencing reads, thereby producing a contiguous nucleotide sequence of a nucleic acid of interest.

With respect to aspects of certain sequencing methods described above, each template nucleic acid includes an adaptor sequence that is complementary to a primer sequence. In other aspects, the plurality of primers includes first primers and second primers, wherein the first primers and the second primers include a different nucleotide sequence. In yet other aspects, the extended strands or the complements include an oligonucleotide tag. In some such aspects, the oligonucleotide tag is complementary to a sequencing primer. In certain aspects, the first modified nucleotide includes d-isoGTP. In some such aspects, the second modified nucleotide includes d-isoCTP.

Certain embodiments of the methods described herein relate to nucleic acid sequencing methods that include the steps of providing a plurality of polynucleotides, generating deletion products from the plurality of nucleotides, providing a substrate having a surface that includes a site having the deletion products attached thereto, amplifying the deletion products on the surface to form amplicons corresponding to the deletion products, and obtaining nucleotide sequence information from nucleic acids present in said amplicons. In some such embodiments, the deletion products include overlapping deletion products.

In some aspects, the sequencing methods further include the step of assembling nucleotide sequence information corresponding to the overlapping deletion products, thereby producing a contiguous nucleotide sequence of a nucleic acid of interest.

In other embodiments, the step of providing the substrate includes hybridizing a plurality of deletion products to a plurality of primers attached to the site. In some aspects, each deletion product includes an adaptor sequence that is complimentary to a primer sequence. In other aspects, the plurality of primers includes first primers and second primers that include a different nucleotide sequence. In still other aspects, the sequencing methods further include extending the primers, thereby producing extended strands.

In other such embodiments, the step of generating deletion products includes extending random primers that hybridize to the polynucleotides and initiate extension at random positions such that the random primers are extended to lengths that are less than the full length of the polynucleotides. In some aspects, the random primers comprise a random hexamer oligonucleotide.

In still other embodiments, the step of generating deletion products includes inserting transposon ends into the polynucleotides. In some such embodiments, inserting transposon ends into the polynucleotides produces fragments of said polynucleotides disposed between said transposon ends. In some aspects, the step of generating deletion products further includes amplifying the fragments that include the ends of the polynucleotides. In other aspects, the step of generating deletion products further includes amplifying the fragments that correspond to internal regions of the polynucleotides.

In some embodiments in which deletion products are generated from a plurality of polynucleotides prior to hybridizing the deletion products to a substrate, polynucleotides corresponding to different nucleic acids of interest can first be attached to different oligonucleotide tags such that subsequently generated deletion products corresponding to different nucleic acids of interest can be grouped or differentiated.

Some embodiments of the above-described sequencing methods relate to provision of a substrate having a surface. In some embodiments, the substrate includes a flow chamber. In some embodiments, the surface of the substrate is planer. In other embodiments, the surface of the substrate is patterned. In still other embodiments, the surface includes a channel in a flow chamber.

Further embodiments of the sequencing methods described above relate to provision of a substrate having a surface comprising sites. In some embodiments, a site can include a well. In some embodiments, sites can include a bead in a well.

In addition to the methods described herein, array compositions for sequencing nucleic acids are described. In some embodiments, an array includes a substrate having a surface that has a site including a plurality of amplicons distributed thereon, wherein each of the plurality of amplicons includes a set of amplified polynucleotides including a deletion product, wherein the deletion product is different for different amplicons, and a sequencing enzyme associated with each of the amplicons.

In certain embodiments, each amplified polynucleotide includes an oligonucleotide tag. In some such embodiments, the oligonucleotide tag is complementary to a sequencing primer.

In some embodiments of the array compositions described herein, the substrate includes a flow chamber. In some embodiments, the surface is planar. In other embodiments, the surface is patterned. In still other embodiments, the surface includes a channel in a flow chamber.

In additional embodiments of the array compositions described herein, the surface of the array substrate includes a site that comprises a well. In some embodiments, the array substrate comprises a plurality of sites comprising a plurality of wells. In some embodiments, the substrate can comprise a bead in a well.

In another embodiment of the array compositions described herein, the sequencing enzyme includes one or more polymerase activities.

Additional embodiments of compositions described herein relate to arrays that comprise a substrate having a surface that has a site including a plurality of amplicons distributed thereon, wherein each of the plurality of amplicons includes a set of amplified polynucleotides, wherein each polynucleotide includes a modified nucleotide incorporated at the same sequence location, and wherein the location is different for different amplicons, and a sequencing enzyme associated with each of the amplicons.

In certain embodiments, each amplified polynucleotide includes an oligonucleotide tag. In some such embodiments, the oligonucleotide tag is complementary to a sequencing primer.

In some embodiments of the array compositions described above, the substrate includes a flow chamber. In some embodiments, the surface is planar. In other embodiments, the surface is patterned. In still other embodiments, the surface includes a channel in a flow chamber.

In additional embodiments of the array compositions described above, the surface of the array substrate includes a site that comprises a well. In some embodiments, the array substrate comprises a plurality of sites comprising a plurality of wells. In some embodiments, the substrate can comprise a bead in a well.

In another embodiment of the array compositions described above, the sequencing enzyme includes one or more polymerase activities.

DETAILED DESCRIPTION

Figure 1:
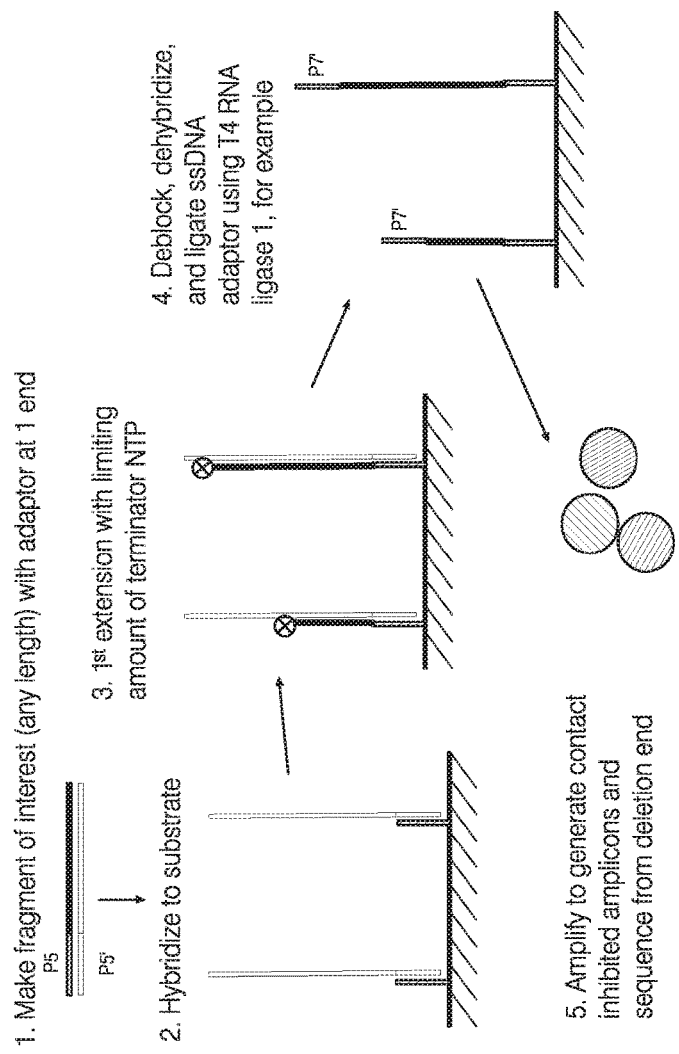
FIG. 1 is a schematic illustration showing a method of generating overlapping sequence reads and obtaining a contiguous nucleotide sequence of a nucleic acid of interest from deletion products formed by extension of capture probes in the presence of terminator nucleotides.

The description that follows illustrates embodiments of the subject matter disclosed herein. Those of skill in the art will recognize that there are numerous variations and modifications of the subject matter provided herein that are encompassed by its scope. Accordingly, the description of a certain embodiments should not be deemed to limit the scope of the present invention.

Embodiments of the present invention relate to methods and array compositions for sequencing molecules, such as nucleic acids. Some embodiments of the methods described herein relate to generating overlapping sequencing reads by producing a set of overlapping nucleotide regions at a site on an array and sequencing those overlapping regions. In some embodiments of these methods, the set of overlapping nucleotide regions is produced by generating a set of overlapping deletion products. In other embodiments of these methods, the set of overlapping nucleotide regions is produced by generating polynucleotides that comprise a modified nucleotide that indicates the beginning of each nucleotide region to be sequenced. Some embodiments of the array compositions described herein relate to arrays comprising a substrate having a surface comprising sites. At least some of these sites comprise a plurality of nucleic acid amplicons, wherein one or more of the amplicons comprises a set of amplified polynucleotides. In some embodiments, the set of amplified polynucleotides comprise deletion product, wherein the deletion product is different for different amplicons. In other embodiments, the set amplified polynucleotides comprise a modified nucleotide, wherein the modified nucleotide is incorporated at the same sequence location, and wherein the sequence location is different for different amplicons. In some embodiments, the array compositions also comprise a sequencing enzyme associated with one or more amplicons.

Target Nucleic Acids

In some embodiments of the methods and compositions described herein, a target nucleic acid can include any nucleic acid of interest. Target nucleic acids can include DNA, RNA, peptide nucleic acid, morpholino nucleic acid, locked nucleic acid, glycol nucleic acid, threose nucleic acid, mixtures thereof, and hybrids thereof. In preferred embodiments, the target nucleic acid is obtained from one or more source organisms. As used herein the term "organism" means any living or self replicating particle that is or was previously in existence. As used herein the term "organism" is not necessarily limited to a particular species of organism but can be used to refer to the living or self replicating particle at any level of classification. For example, the term "organism" can be used to refer collectively to all of the species within the genus *Salmonella* or all of the bacteria within the kingdom Eubacteria.

A target nucleic acid can comprise any nucleotide sequence. In some embodiments, the target nucleic acid can comprise a selected sequence or a portion of a larger sequence. In some embodiments, sequencing a portion of a target nucleic acid or a fragment thereof can be used to identify the source of the target nucleic acid. In some embodiments, particular genes or regions of a genome may or may not be sequenced.

Some embodiments described herein can utilize a single target nucleic acid. Other embodiments can utilize a plurality of target nucleic acids. In such embodiments, a plurality of target nucleic acids can include a plurality of the same target nucleic acids, a plurality of different target nucleic acids where some target nucleic acids are the same, or a plurality of target nucleic acids where all target nucleic acids are different. In some embodiments, the plurality of target nucleic acids can include substantially all of a particular organism's genome. In some embodiments, the plurality of target nucleic acids can include at least a portion of a particular organism's genome including, for example, at least about 10%, 25%, 50%, 75%, 80%, 85%, 90%, 95%, or 99% of the genome. In other embodiments, the plurality of target nucleic acids can include a single nucleotide sequence of the genome of an organism or a single expressed nucleotide sequence. In still other embodiments, the plurality of target nucleic acids can include a portion of a single nucleotide sequence of the genome of an organism or a portion of a single expressed nucleotide sequence. With reference to nucleic acids, polynucleotides and/or nucleotide sequences a "portion," "fragment" or "region" can be at least 5 consecutive nucleotides, at least 10 consecutive nucleotides, at least 15 consecutive nucleotides, at least 20 consecutive nucleotides, at least 25 consecutive nucleotides, at least 50 consecutive nucleotides or at least 100 consecutive nucleotides.

Target nucleic acids can be obtained from any source. For example, target nucleic acids may be prepared from nucleic acid molecules obtained from a single organism or from populations of nucleic acid molecules obtained from natural sources that include one or more organisms. Sources of nucleic acid molecules include, but are not limited to, organelles, cells, tissues, organs, or organisms. Cells that may be used as sources of target nucleic acid molecules may be prokaryotic (bacterial cells, e.g., *Escherichia, Bacillus, Serratia, Salmonella, Staphylococcus, Streptococcus, Clostridium, Chlamydia, Neisseria, Treponema, Mycoplasma, Borrelia, Legionella, Pseudomonas, Mycobacterium, Helicobacter, Erwinia, Agrobacterium, Rhizobium,* and *Streptomyces* genera); archeaon, such as crenarchaeota, nanoarchaeota or euryarchaeotia; or eukaryotic such as fungi, (e.g., yeasts), plants, protozoans and other parasites, and animals (including insects (e.g., *Drosophila* spp.), nematodes (e.g., *Caenorhabditis elegans*), and mammals (e.g., rat, mouse, monkey, non-human primate and human)).

In some embodiments, a target nucleic acid can be obtained from a specific biological source. In a preferred embodiment, the target nucleic acid is human nucleic acid obtained from a human, for example a sample of human tissue. In other embodiments, the target nucleic acid is a human mitochondrial nucleic acid. In other embodiments, the nucleic acid can be obtained from a metagenomic sample. In other embodiments, the target nucleic acid can be obtained from an environmental source that no longer comprises living organisms.

Target Nucleic Acid Preparation

In several embodiments, a target nucleic acid can be processed by standard molecular biology techniques for downstream applications. In particular embodiments, target nucleic acids can be prepared from fragmented polynucleotides. The fragments are subsequently attached to an adaptor polynucleotide sequence. In some embodiments, the adaptor polynucleotide sequence is double-stranded. In some embodiments, the fragments are end repaired prior to attaching to the adaptor polynucleotide sequences. Adaptor polynucleotides can be attached to one or both ends of the fragmented nucleotide sequences. It will be appreciated that the same or different adaptor can be bound to each end of the fragment, thereby producing an "adaptor-fragment-adaptor" construct. It will also be appreciated that a plurality of the same or different adaptor can be bound to each end of the fragment. In preferred embodiments, different adaptors are attached to each end of the fragment when adaptors are attached to both ends of the fragment. Methods of attaching nucleic acid adaptors to a nucleic acid of interest are well known in the art. Particularly, ligation methods are known in the art using standard molecular cloning techniques (Sambrook and Russell, Molecular Cloning, A Laboratory Manual, $3^{rd}$ edition Cold Spring Harbor Laboratory Press (2001), herein incorporated by reference).

In some embodiments, the adaptor constructs may contain a mismatched region on one or both of the strands that does not hybridize with a sequence on the other strand of the adaptor, and act as amplification priming sites. Additionally, adaptor-fragment-adaptor constructs can be amplified by standard amplification reactions generally involving forward and reverse oligonucleotide primers that can anneal to at least a portion of the adaptors. Forward and reverse amplification primers may also extend beyond the adaptors. It will be appreciated by one of ordinary skill in the art that forward and reverse primer sequences do not need to be perfectly complementary to their primer-binding sequence of the template. Primers can be designed having a suitable number of mismatched bases against the template and still exhibit an appropriate level of specific annealing to the template. In various embodiments, a target nucleic acid having one or two duplex adaptors attached to its end(s) is amplified prior to hybridization to a substrate.

In some embodiments, an oligonucleotide tag complementary to a sequencing primer can be incorporated with adaptors attached to a target nucleic acid. For analysis of multiple samples, different oligonucleotide tags complementary to separate sequencing primers can be incorporated with adaptors attached to a target nucleic acid.

In some embodiments, an oligonucleotide index tag can be incorporated with adaptors attached to a target nucleic acid. In embodiments in which deletion products are generated from a plurality of polynucleotides prior to hybridizing the deletion products to a substrate, polynucleotides corresponding to different nucleic acids of interest can first be attached to different oligonucleotide tags such that subsequently generated deletion products corresponding to different nucleic acids of interest can be grouped or differentiated. Consequently, in various embodiments, deletion products derived from the same nucleic acid of interest will have the same oligonucleotide index tag such that the index tag identifies sequencing reads derived from the same nucleic acid of interest. Likewise, deletion products derived from different nucleic acids of interest will have different oligonucleotide index tags to allow them to be grouped or differentiated such as on a substrate. Oligonucleotide index tags may range in length from about 5, 10, 15, 20, 25, 30, 35, 40, 45, 50, 75, to 100 nucleotides or basepairs, or any length in between.

In some embodiments, the oligonucleotide index tags are not added in conjunction with the adaptors, but rather, are added separately or in conjunction with a primer, primer binding site or other component. In other embodiments, no index tag is used, but rather, a pair-end read is performed. The read from the first end comprises a portion of the sequence of interest and the read from the other (second) end is utilized as a tag to identify the fragment from which the first read originated.

Converting Double-Stranded Nucleic Acids to Single-Stranded Nucleic Acids

Some embodiments of the present invention relate to converting double-stranded nucleic acids to single-stranded nucleic acids. In a variety of embodiments, methods of obtaining a contiguous nucleotide sequence of a nucleic acid of interest are provided. Single-stranded nucleic acids can be generated corresponding to the nucleic acid of interest. As used herein, "nucleic acid" includes both DNA and RNA. In some embodiments, the term "nucleic acid" includes DNA and RNA comprising one or more modified nucleobases or nucleobase analogs. Modified nucleic acids are nucleic acids having nucleotides or structures which may or may not occur in nature. For example, methylation of DNA bases are modifications that often occur in nature, whereas aminations of nucleobases typically do not. Double-stranded nucleic acids can include double-stranded DNA, double-stranded RNA and double-stranded DNA/RNA hybrid molecules. Double-stranded nucleic acids can be denatured or converted to single-stranded nucleic acids by a variety of methods. These methods can include chemical methods, for example, by the addition of chaotropic agents, such as urea, to induce double-stranded nucleic acids to separate into single-stranded molecules. Other methods include physical means, such as heating to a temperature sufficient to disrupt the hydrogen bonding between the two strands of the double-stranded nucleic acids. Still other methods include employing one or more enzymes, such as nucleases, to preferentially digest one of the strands of the double-stranded nucleic acid, thereby leaving an undigested single strand. Furthermore, double-stranded nucleic acid can be converted to a single-stranded nucleic acid by treatment with an enzyme or other reagent that degrades one strand. Enzymatic or chemical treatment can occur under conditions that are not sufficient to disrupt the hydrogen bonding between the two strands of the double-stranded nucleic acids when not in the presence of the degrading reagent or enzyme. For example, the temperature can be sufficiently low that the double-stranded nucleic acid remains hybridized absent the degrading reagent or enzyme. Also, the chemical conditions can be such that the hybrid is not substantially disrupted absent the degrading reagent or enzyme.

The methods exemplified herein for converting double-stranded nucleic acids to single-stranded nucleic acids are also applicable to converting a double-stranded nucleic acid region to a region that is single-stranded. Thus, the methods can be used to produce a nucleic acid having a single-stranded region that is of sufficient length to hybridize to a capture probe or other nucleic acid. In other words, a double-stranded nucleic acid region can be retained in a nucleic acid that is converted to have a single-stranded region in a method of the invention. For example, a nuclease can digest a portion of one strand in a double-stranded nucleic acid such that the product has both a double-stranded region and a single-stranded region. Such molecules can be referred to as partial duplexes.

There are a variety of nucleases that can be used to digest one strand of a double-stranded nucleic acid, so as to form a single-stranded nucleic acid. Examples of such nucleases include, but are not limited to, lambda exonuclease, exonuclease III, and T7 exonuclease.

In preferred embodiments, a double-stranded nucleic acid can be converted to a single-stranded nucleic acid using lambda exonuclease. Lambda exonuclease is a highly processive exodeoxyribonuclease that selectively digests the 5'-phosphorylated strand of double-stranded DNA in a 5' to 3' direction. The enzyme exhibits greatly reduced activity on single-stranded DNA and non-phosphorylated DNA, and has no activity at nicks and limited activity at gaps in DNA (Little, J. W., An exonuclease induced by bacteriophage lambda: II, Nature of the enzymatic reaction, J. Biol. Chem., 242, 679-686, 1967; Mitsis, P. G., Kwagh, J. G., Characterization of the interaction of lambda exonuclease with the ends of DNA, Nucleic Acids Res., 27, 3057-3063, 1999).

Additional nucleases for converting a double-stranded nucleic acid to a single-stranded nucleic acid include exonuclease III. Exonuclease III catalyzes the stepwise removal of mononucleotides from 3'-hydroxyl termini of duplex DNA (Rogers, G. S. and Weiss, B. (1980) L. Grossman and K. Moldave (Eds.), *Methods Enzymol.,* 65, pp. 201-211. New York: Academic Press). During each binding event, only a limited number of nucleotides are removed, resulting in coordinated progressive deletions within the population of DNA molecules (Sambrook, J., Fritsch, E. F. and Maniatis, T. (1989) *Molecular Cloning: A Laboratory Manual* (2nd. Ed.), 5.84-5.85). Although the enzyme also acts at nicks in duplex DNA to produce single-strand gaps, the preferred substrates are blunt or recessed 3'-termini. The enzyme is not active on single-stranded DNA, and thus 3'-protruding termini are resistant to cleavage. The degree of resistance depends on the length of the extension, with extensions 4 bases or longer being essentially resistant to cleavage. Temperature, salt concentration and the ratio of enzyme to DNA can affect enzyme activity, thus reaction conditions can be tailored to specific applications. Exonuclease III may also have RNase H, 3'-phosphatase and AP-endonuclease activities (Rogers, G. S. and Weiss, B. (1980) L. Grossman and K. Moldave (Eds.), *Methods Enzymol.,* 65, pp. 201-211. New York: Academic Press).

Still other nucleases for converting a double-stranded nucleic acid to a single-stranded nucleic acid include T7 exonuclease. T7 Exonuclease acts in the 5' to 3' direction, catalyzing the removal of 5' mononucleotides from duplex DNA. T7 Exonuclease initiates nucleotide removal from the 5' termini or at gaps and nicks of double-stranded DNA (Kerr, C. and Sadowski, P. D. (1972) *J. Biol. Chem.,* 247, 305-318). It will degrade both 5' phosphorylated or 5' dephosphorylated DNA. The enzyme may also degrade RNA and DNA from RNA/DNA hybrids in the 5' to 3' direction (Shinozaki, K. and Okazaki, T. (1978) *Nucl. Acids Res.,* 5, 4245-4261).

Nucleases that specifically recognize RNA/DNA hybrids can also be used to promote strand conversion. For example, RNase H is a nuclease that specifically recognizes RNA/DNA hybrids and specifically degrades the RNA. Because RNase H does not degrade DNA it can be used to convert double-stranded DNA/RNA hybrids to single-stranded DNA molecules. RNase H is often used to destroy the RNA template after first-strand cDNA synthesis and in nuclease protection assays. RNase H can also be used to degrade specific RNA strands when a DNA oligonucleotide is hybridized, such as in the removal of the poly(A) tail from mRNA hybridized to oligo(dT) or the destruction of specific RNA molecules inside or outside the living cell.

Buffered Solutions

In some embodiments of the present invention, different reactions may occur in different buffered solutions. In other embodiments, different reactions may occur in substantially the same or a similar buffered solution. In such embodiments, substantially the same buffered solution refers to a reaction solution in which a series of reactions can occur. In some embodiments, the concentration of certain reaction components and the volume of the buffered solution used in a second reaction can vary from the concentration of certain reaction components and the volume of the buffered solution used in a first reaction. The variation may be insubstantial, for example, less than 25%, more preferably less than 15%, even more preferably less than 5%, thereby resulting in substantially the same buffer solutions. In other embodiments, the concentration of certain reaction components and the volume of the buffered solution used in the second reaction can vary considerably from the concentration of certain reaction components and the volume of the buffered solution used in the first reaction. The variation can be, for example, more than 25%, more than 50%, more than 75% or even more than 100%.

A variety of buffered solutions can be used with the methods and compositions described herein. Typically, the buffered solutions contemplated herein are made from a weak acid and its conjugate base or a weak base and its conjugate acid. For example, sodium acetate and acetic acid are buffer agents that can be used to form an acetate buffer. Other examples of buffer agents that can be used to make buffered solutions include, but are not limited to, Tris, Tricine, HEPES, TES, MOPS, MOPSO and PIPES. Additionally, other buffer agents that can be used in enzyme reactions, hybridization reactions, and detection reactions are well known in the art. In preferred embodiments, the buffered solution can include Tris.

With respect to the embodiments described herein, the pH of the buffered solution can be modulated to permit any of the described reactions. In some embodiments, the buffered solution can have a pH greater than pH 2.0, greater than pH 2.5, greater than pH 3.0, greater than pH 3.5, greater than pH 4.0, greater than pH 4.5, greater than pH 5.0, greater than pH 5.5, greater than pH 6.0, greater than pH 6.5, greater than pH 7.0, greater than pH 7.5, greater than pH 8.0, greater than pH 8.5, greater than pH 9.0, greater than pH 9.5, greater than pH 10, greater than pH 10.5, greater than pH 11.0, greater than pH 11.5 or greater than pH 12.0. Additionally or alternatively the pH can be less than 12.0, less than 11.5, less than 11.0, less than 10.5, less than 10.0, less than 9.5, less than 9.0, less than 8.5, less than 8.0, less than 7.5, less than 7.0, less than 6.5, less than 6.0, less than 5.5, less than 5.0, less than 4.5, less than 4.0, less than 3.5, less than 3.0, or less than 2.5. In other embodiments, the buffered solution can have a pH ranging, for example, from about pH 2 to about pH 12, from about pH 4 to about pH 10, from about pH 5 to about pH 9, from about pH 6 to about pH 9 or from about pH 7 to about pH 9.

In preferred embodiments, the buffered solution can comprise one or more divalent cations. Examples of divalent cations can include, but are not limited to, $Mg^{2+}$, $Mn^{2+}$, $Zn^{2+}$ and $Ca^{2+}$. In preferred embodiments, the buffered solution can contain one or more divalent cations at a concentration sufficient to permit hybridization of a single-stranded nucleic acid complementary to a capture probe. In some embodiments, a concentration sufficient to permit hybridization of a single-stranded nucleic acid complementary to a capture probe can be more than about 1 μM, more than about 2 μM, more than about 5 μM, more than about 10 μM, more than about 25 μM, more than about 50 μM, more than about 75 μM, more than about 100 μM, more than about 200 μM, more than about 300 μM, more than about 400 μM, more than about 500 μM, more than about 750 μM, more than about 1 mM, more than about 2 mM, more than about 5 mM, more than about 10 mM, more than about 20 mM, more than about 30 mM, more than about 40 mM, more than about 50 mM, more than about 60 mM, more than about 70 mM, more than about 80 mM, more than about 90 mM, more than about 100 mM, more than about 150 mM, more than about 200 mM, more than about 250 mM, more than about 300 mM, more than about 350 mM, more than about 400 mM, more than about 450 mM, more than about 500 mM, more than about 550 mM, more than about 600 mM, more than about 650 mM, more than about 700 mM, more than about 750 mM, more than about 800 mM, more than about 850 mM, more than about 900 mM, more than about 950 mM or more than about 1M.

In some embodiments, the buffered solution can comprise one or more polyamines. Examples of polyamines include, but are not limited to, spermine and spermidine. In preferred embodiments, a buffered solution can comprise one or more polyamines at a concentration at a concentration sufficient to permit hybridization of a single-stranded nucleic acid complementary to a capture probe. In some embodiments, a concentration sufficient to permit hybridization of a single-stranded nucleic acid complementary to a capture probe can be more than about 1 μM, more than about 2 μM, more than about 5 μM, more than about 10 μM, more than about 25 μM, more than about 50 μM, more than about 75 μM, more than about 100 μM, more than about 200 μM, more than about 300 μM, more than about 400 μM, more than about 500 μM, more than about 750 μM, more than about 1 mM, more than about 2 mM, more than about 5 mM, more than about 10 mM, more than about 20 mM, more than about 30 mM, more than about 40 mM, more than about 50 mM, more than about 60 mM, more than about 70 mM, more than about 80 mM, more than about 90 mM, more than about 100 mM, more than about 150 mM, more than about 200 mM, more than about 250 mM, more than about 300 mM, more than about 350 mM, more than about 400 mM, more than about 450 mM, more than about 500 mM, more than about 550 mM, more than about 600 mM, more than about 650 mM, more than about 700 mM, more than about 750 mM, more than about 800 mM, more than about 850 mM, more than about 900 mM, more than about 950 mM or more than about 1M. In other embodiments, the buffered solution can comprise both one or more divalent cations and one or more polyamines.

In a preferred embodiment, the buffered solution comprises one or more divalent cations and/or one or more polyamines and lacks monovalent cations and phosphate ions.

Hybridization

Some embodiments of the present invention relate to hybridization between single-stranded nucleic acids and capture probes. In some embodiments, the capture probes are primers that are attached to the surface of an array substrate. In some embodiments, the capture probes are attached to the surface of the array substrate and can serve as primers in addition to functioning as a capture probe. As described further herein, capture probes can be short nucleic acids or oligonucleotides. Short nucleic acids typically have a length of 1000 nucleotide or less. In a preferred embodiment, the length of a capture probe ranges from about 10 nucleotides to about 100 nucleotides. In a more preferred embodiment, the length of a capture probe can be less than 50 nucleotides. In an even more preferred embodiment, the length of a capture probe range from about 20 to 40 nucleotides. Other embodiments of the present invention relate to hybridization between single-stranded nucleic acids and other nucleic acid molecules having a length greater than 1000 base pairs. Several useful properties of single-stranded nucleic acids are exemplified below. It will be understood that a single-stranded region of a nucleic acid can have similar useful properties even if the nucleic acid also has a double-stranded region. As such, it will be appreciated that in some embodiments, hybridization can occur between partial two or more partial duplex molecules.

Hybridization occurs when hydrogen bonds form between complementary nucleotide bases, for example, T-A, C-G, and A-U. Complementary nucleic acids comprise complementary bases with the capacity for precise pairing between two nucleotides, for example, if a nucleotide at a certain position in the sequence of nucleotides of an single-stranded nucleic acid is capable of hydrogen bonding with a nucleotide at the same position in the sequence of nucleotides of a capture probe, then the single-stranded nucleic acid and capture probe are considered to be complementary to each other at that position. The single-stranded nucleic acid and the capture probe are complementary to each other when a sufficient number of corresponding positions in each molecule are occupied by nucleotides which can hydrogen bond with each other. Accordingly, complementary does not necessarily mean that two hybridizing nucleic acid stranded have 100% nucleotide complementarity in the hybridizing region. For example, in some embodiments, hybridizing nucleic acids can have less than 100% complementarity, less than 99% complementarity, less than 98% complementarity, less than 97% complementarity, less than 96% complementarity, less than 95% complementarity, less than 94% complementarity, less than 93% complementarity, less than 92% complementarity, less than 91% complementarity, less than 90% complementarity, less than 89% complementarity, less than 88% complementarity, less than 87% complementarity, less than 86% complementarity, less than 85% complementarity, less than 84% complementarity, less than 83% complementarity, less than 82% complementarity, less than 81% complementarity, less than 80% complementarity, 79% complementarity, less than 78% complementarity, less than 77% complementarity, less than 76% complementarity, less than 75% complementarity, less than 74% complementarity, less than 73% complementarity, less than 72% complementarity, less than 71% complementarity or less than 70% complementarity in the hybridizing region provided that the complementarity is sufficient to promote hybridization under the conditions used. In preferred embodiments, the hybridization occurs between specific complementary sequences and not between non-complementary sequences.

The ability of a single-stranded nucleic acid and a capture probe to hybridize to one another can be affected by the number of complementary nucleotides and the relative positions of those complementary nucleotides in the single-stranded nucleic acid and capture probe. For example, a single-stranded nucleic acid containing a greater number of complementary nucleotides in a contiguous sequence can have a higher degree of complementarity than a single-stranded nucleic acid contains a lower number of complementary nucleotides with non-complementary nucleotides dispersed therein. In addition, as indicated above, the ability of a single-stranded nucleic acid and capture probe to hybridize to one another can be modulated by varying the conditions in which the hybridization occurs.

In some embodiments of the methods and compositions described herein, a single-stranded nucleic acid can contain at least one sequence that can hybridize to a sequence contained in a capture probe. Such sequences that can hybridize include complementary nucleotides. In certain embodiments, a sequence that can hybridize can contain a contiguous sequence of complementary nucleotides. For example, a single-stranded nucleic acid can contain at least one contiguous sequence complementary to at least one sequence in capture probe. In such embodiments, the at least one contiguous sequence of complementary nucleotides contained in the capture probe and/or single-stranded nucleic acid can have a length of at least 5 nucleotides, at least 6 nucleotides, at least 7 nucleotides, at least 8 nucleotides, at least 9 nucleotides, at least 10 nucleotides, at least 11 nucleotides, at least 12 nucleotides, at least 13 nucleotides, at least 14 nucleotides, at least 15 nucleotides, at least 16 nucleotides, at least 17 nucleotides, at least 18 nucleotides, at least 19 nucleotides, at least 20 nucleotides, at least 21 nucleotides, at least 22 nucleotides, at least 23 nucleotides, at least 24 nucleotides, at least 25 nucleotides, at least 26 nucleotides, at least 27 nucleotides, at least 28 nucleotides, at least 29 nucleotides, at least 30 nucleotides, at least 31 nucleotides, at least 32 nucleotides, at least 33 nucleotide, at least 34 nucleotides, at least 35 nucleotides, at least 36 nucleotides, at least 37 nucleotides, at least 38 nucleotides, at least 39 nucleotides, at least 40 nucleotides, at least 41 nucleotides, at least 42 nucleotides, at least 43 nucleotides, at least 44 nucleotides, at least 45 nucleotides, at least 46 nucleotides, at least 47 nucleotides, at least 48 nucleotides, at least 49 nucleotides, at least 50 nucleotides, at least 51 nucleotides, at least 52 nucleotides, at least 53 nucleotides, at least 54 nucleotides, at least 55 nucleotides, at least 56 nucleotides, at least 57 nucleotides, at least 58 nucleotides, at least 59 nucleotides, at least 60 nucleotides, at least 61 nucleotides, at least 62 nucleotides, at least 63 nucleotides, at least 64 nucleotides, at least 65 nucleotides, at least 66 nucleotides, at least 67 nucleotides, at least 68 nucleotides, at least 69 nucleotides, at least 70 nucleotides, at least 71 nucleotides, at least 72 nucleotides, at least 73 nucleotides, at least 74 nucleotides or at least 75 nucleotides.

In other embodiments, the sequence that can hybridize to another sequence can contain non-complementary nucleotides. In such embodiments, a sequence that can hybridize can contain 1 non-complementary nucleotide, 2 non-complementary nucleotides, 3 non-complementary nucleotides, 4 non-complementary nucleotides, 5 non-complementary nucleotides, 6 non-complementary nucleotides, 7 non-complementary nucleotides, 8 non-complementary nucleotides, 9 non-complementary nucleotides, 10 non-complementary nucleotides, 11 non-complementary nucleotides, 12 non-complementary nucleotides, 13 non-complementary nucleotides, 14 non-complementary nucleotides, 15 non-complementary nucleotides, 16 non-complementary nucleotides, 17 non-complementary nucleotides, 18 non-complementary nucleotides, 19 non-complementary nucleotides, 20 non-complementary nucleotides, 25 non-complementary nucleotides, 30 non-complementary nucleotides, 35 non-complementary nucleotides, 40 non-complementary nucleotides, 45 non-complementary nucleotides, or 50 non-complementary nucleotides.

As is known in the art, the ability of a single-stranded nucleic acid and capture probe to hybridize to one another can be modulated by varying the conditions in which the hybridization occurs. Such conditions are well known in the art and can include, for example, pH, temperature, concentration of salts, and the presence of particular molecules in the hybridization reaction. Under conditions of low stringency, a capture probe and single-stranded nucleic acid with a low degree of complementarity may be able to hybridize to one another. Conversely, under more highly stringent conditions, only capture probes and single-stranded nucleic acids with a high degree of complementarity are likely to hybridize to one another.

In certain embodiments, hybridization of the single-stranded nucleic acid and capture probe can be made to occur under conditions with high stringency. One condition that greatly affects stringency is temperature. In general, increasing the temperature at which the hybridization is performed increases the stringency. As such, the hybridization reactions described herein can be performed at a different temperature depending on the desired stringency of hybridization. For example, hybridization can be performed at a temperature ranging from 15° C. to 95° C. In some embodiments, the hybridization is performed at a temperature of about 20° C., about 25° C., about 30° C., about 35° C., about 40° C., about 45° C., about 50° C., about 55° C., about 60° C., about 65° C., about 70° C., about 75° C., about 80° C., about 85° C., about 90° C., or about 95° C. In other embodiments, the stringency of the hybridization can further altered by the addition or removal of components of the buffered solution.

In particular embodiments, a probe, such as a capture probe, can be resistant to exonuclease degradation. For example the probe can have a non natural backbone that can not be cleaved by a particular exonuclease such as a protein nucleic acid backbone. A probe can include a blocking group that prevents or inhibits exonuclease degradation. For example, a blocking group can present at the 3' end of a probe or at the 5' end of the probe. A blocking group at the 3' end can prevent degradation of the probe by exonuclease III. A blocking group at the 5' end can prevent degradation of the probe by lambda exonuclease or T7 exonuclease.

Deletion Product Generation

Several embodiments of the methods and compositions described herein involve producing a set of overlapping sequence reads. In various embodiments, nucleic acid sequencing methods involve generating deletion products from polynucleotides attached to a site on a surface of a substrate. In several other embodiments, nucleic acid sequencing methods involve generating deletion products from polynucleotides prior to attachment to a site on a surface of a substrate.

In some embodiments, nested deletion fragments of a nucleotide of interest are generated. In some embodiments, "nested deletions," "nested deletion fragments," or "deletion products" refer to overlapping nucleotide regions of a template nucleic acid. Any means of producing nested deletions known in the art are suitable for the embodiments of the present invention including, but not limited to, physical shearing (e.g. mechanical fragmentation), chemical fragmentation, thermal fragmentation, and enzymatic fragmentation. Any of the aforementioned methods of producing nested deletions can be performed on or off the surface of a substrate.

In some embodiments of the methods described herein, single-stranded template nucleic acids are hybridized to capture probes attached to the surface of a substrate, such as a solid support. In some embodiments, single-stranded template nucleic acids are attached directly, or through a linker molecule, to the surface of a substrate rather than through a capture probe.

In certain embodiments, deletion products are generated from single-stranded template nucleic acids. In some such embodiments, deletion products are generated during extension of capture probes hybridized to a single-stranded template nucleic acid. In other such embodiments, deletion products are generated after extension of capture probes hybridized to a single-stranded template nucleic acid, whether before or after amplification of the extended capture probes.

In other embodiments, overlapping deletion products are generated by incompletely extending capture probes such that capture probes are extended to lengths that are less than the full length of the template nucleic acid. Any means of incompletely extending the capture probes may be employed.

In several embodiments, capture probes are extended in the presence of one or more terminator nucleotides. A terminator nucleotide is incorporated during capture probe extension and prevents further extension. In various embodiments, a limiting amount of terminator nucleotide is added to a capture probe extension reaction such that it is incorporated at different nucleotide positions among a plurality of capture probes being extended. Overlapping deletion products are formed by virtue of termination of capture probe extension at various lengths less than the full length of the template nucleic acid. In preferred embodiments, the terminator nucleotide is reversible and can be unblocked or removed, permitting further extension, attachment of a nucleic acid adaptor, and/or amplification (e.g. bridge amplification). Reversible terminators are known in the art, examples of which are described in U.S. Pat. Nos. 7,541,444; 7,057,026; 7,414,116; 7,427,673; 7,566,537; 7,592,435 and WO 07/135368, each of which is incorporated herein by reference in its entirety. As another example, US 2006/0160081, herein fully incorporated by reference, describes nucleotides comprising a purine or pyrimidine base and a ribose or deoxyribose sugar moiety which has an attached removable blocking group. US 2007/0166705, herein fully incorporated by reference, describes modified nucleotides having removable 3'-OH blocking groups, which can be used for controlled incorporation of nucleotides in a stepwise manner.

In some embodiments, incomplete capture probe extension is accomplished by extending capture probes in the presence of uracil, such that the capture probes are extended to lengths less than the full length of the template nucleic acid. This can be accomplished, for example, by cleaving at the point of uracil incorporation with Uracil-DNA Glycosylase followed by heating or followed by treatment with Endonuclease VIII. A commercially available mixture of Uracil-DNA Glycosylase and Endonuclease VIII, known as USER™ is available from New England Biolabs (Ipswich, Mass.).

In other embodiments, capture probes hybridized to template nucleic acid are fully extended prior to generation of overlapping deletion products. It will be appreciated that extended capture probes can optionally be amplified, such as by bridge amplification, prior to generation of overlapping deletion products. In some embodiments, overlapping deletion products are generated by enzymatic digestion of extended capture probes. In one embodiment, extended capture probes attached at a site on a surface of a substrate are amplified and their free ends are digested with a nuclease to generate a set of deletion products of varying lengths having overlapping regions with respect to their digested free ends. In preferred embodiments, exonucleases are used to digest the free ends of extended capture probes. Any exonuclease, including but not limited to exonuclease I, II, III, IV, V, VI, VII, and VIII, can be used in various embodiments to generate overlapping deletion products. In other preferred embodiments, endonucleases such as DNase I are used to randomly cleave the extended capture probes. It will be appreciated that adaptors can be attached to the free ends of the overlapping deletion fragments for amplification and sequencing. For example, a single-stranded adaptor can be ligated to the extended probes of varying length, which can be amplified (e.g. by cluster/bridge amplification), sequenced, and assembled to provide the contiguous nucleotide sequence of the nucleic acid of interest.

In other embodiments, overlapping deletion products are produced by restriction enzymes, nicking enzymes, chemical cleavage, cleavage of abasic sites with enzymes (e.g.

New England Biolab's USER™ digest), exposure to heat or alkali, cleavage of ribonucleotides incorporated into amplification products otherwise comprised of deoxyribonucleotides, or photochemical cleavage.

In certain embodiments of the present invention, overlapping deletion products are produced by physically shearing nucleic acids into fragments. Any means of physically shearing nucleic acids is suitable, including but not limited to sonication or nebulization of nucleic acids. In several embodiments, a plurality of capture probes hybridized to template nucleic acid are extended and optionally amplified, such as by bridge amplification on a substrate. These extended capture probes are physically sheared, such as by sonication, which creates random breakpoints. A plurality of capture probes or extended capture probes having random breakpoints at various positions with respect to one another represents a set of overlapping deletion fragments. It will be understood that adaptors can be attached to the free ends (i.e. breakpoints) of the overlapping deletion fragments for amplification and sequencing.

In other embodiments, overlapping deletion products are formed from double-stranded polynucleotides involving nick translation to less than the full length of the polynucleotides. In some embodiments, the double-stranded polynucleotides are the extended capture probes hybridized to template nucleic acid. Nicks can be generated on the extended capture probes, for example by an endonuclease such as DNase I, and translated by a polymerase having 5' to 3' exonuclease activity (e.g. pol I). Translation can be terminated prior to full length translation by any of a variety of means, for example by inactivating the polymerase or incorporating a terminator nucleotide. In preferred embodiments, termination of translation does not interfere with downstream applications such as adaptor attachment to the ends of partially nick-translated nucleotide ends, amplification, or sequencing.

In several embodiments, overlapping deletion products are generated prior to attachment to a site on a surface of a substrate. For example, overlapping deletion products can be generated from template nucleic acids in solution prior to hybridization to capture probes attached to the surface of a substrate, such as the surface of a solid support, or prior to attachment to the surface of a substrate (e.g. via a linker molecule).

In one such embodiment, deletion products are formed by polymerase extension of random primers hybridized to a template nucleic acid. For example, primers having a random nucleotide sequence (e.g. random hexamer primers) and optionally a sequencing primer site and/or adaptor oligonucleotide sequence are incubated with template nucleic acid. Different length single-stranded extension products (e.g. deletion products) are generated based on random priming and initiation of polymerase-mediated extension at various positions with respect to the template nucleic acid. Such deletion products can subsequently be attached to a substrate for downstream applications including amplification and sequencing.

In another such embodiment, deletion products are formed by random fragmentation of double-stranded template nucleic acid using transposon ends appended to sequencing primer sites. For example, transposase catalyzes random insertion of the transposon ends appended to sequencing primer sites at various positions in double-stranded template nucleic acid, which can be flanked by a double-stranded adaptor at both ends. A transposase enzyme induces fragmentation of the template during cut-and-paste transposition by covalent attachment of the 3' ends of the transposons to the 5' end(s) of the fragments. The sizes of the fragments produced can be controlled by adjusting the amount of transposon ends and transposase used in the reaction. Accordingly, fragments of at least about, about or not more than about 5, 10, 25, 50, 75, 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 950, 975, 1000, 1500, 2000, or about 2500 nucleotides or any number in between any of these sizes can be generated. An appropriate amount of transposon ends and transposase can be determined for generating a desired fragment size distribution taking into account the characteristics of the template nucleic acid (e.g. high number of repetitive nucleotide sequences) or factors involving downstream applications such as the read length capacity of the sequencing-by-synthesis method and the number of sequencing cycles desired for assembling the contiguous nucleotide sequence of the template nucleic acid.

In several embodiments, deletion products corresponding to transposon-generated end fragments of a template nucleic acid are generated. In some such embodiments, fragments of various lengths with respect to the ends of the template can be enriched by PCR amplification. In such a reaction, amplification can be performed using at least two types of primers: (1) primers complementary to the aforementioned adaptor and (2) primers, which are complementary to a sequencing primer site, and which are appended to an adaptor oligonucleotide. In some embodiments, the adaptor oligonucleotide appended to this type of primer has a sequence that is different from the adaptor present at the opposite end of the fragment. In some embodiments, the amplification reaction further includes a third type of primer which is complementary to the sequencing primer sites but is not appended to an adaptor oligonucleotide. In various embodiments, the adaptors used are compatible with amplification on the surface of a substrate (e.g. bridge PCR).

In other embodiments, deletion products corresponding to internal fragments flanked by transposon ends are generated. In some such embodiments, both transposon-generated end fragments and transposon-generated internal fragments are produced and enriched. For example, transposon-based fragments can be produced as described above. However, in the present embodiments, both end fragments as well as internal fragments are enriched by PCR amplification. In such a reaction, the end fragments are amplified as described above, and internal fragments, which are tagged at their ends with transposon-sequencing primer sites, are amplified using forward and reverse primers, which are complementary to the sequencing primer sites, and which are appended to an adaptor oligonucleotide. In preferred embodiments, two different sequencing primer sites are utilized and appended to transposon ends such that transposase induces generation of a set of internal fragments tagged with different sequencing primer sites at each end and a set of internal fragments tagged with the same sequencing primer sites at each end. In a preferred embodiment, the set of internal fragments tagged with different sequencing primer sites at each end is enriched over the set of internal fragments tagged with the same sequencing primer sites at each end, for example by suppression PCR amplification. In such a reaction, amplification of internal fragments tagged with the same sequencing primer sites at each end is suppressed. Without being bound by theory, this suppression may be caused by formation of a hairpin structure by the common sequencing primers sites at each end of a fragment.

It will be understood that any of the foregoing embodiments involving generation of overlapping deletion products can be applied to solid phase platforms. In a variety of embodiments, overlapping deletion products are preferably attached to a site on a surface of a substrate. In some preferred embodiments, polynucleotides used to generate the overlapping deletion products are attached to the site on the surface of the substrate prior to generating the deletion products. In other preferred embodiments, deletion products are generated before attaching them to the site on the surface of the substrate.

Initiating Sequencing Reads from Point of Incorporation of Modified Nucleotides

Some embodiments are drawn to sequencing methods involving initiation of a sequencing read from the point of incorporation of a modified nucleotide. Capture probes can be extended in the presence of a first modified nucleotide, such as d-isoGTP or d-isoCTP, with an enzyme capable of incorporating isoguanosine (isoG) or isocytosine (isoC) during extension. For example, the Klenow fragment of pol I is known to carry out a percentage of misincorporation of isoG against a templated T base. Complements of the extended capture probes can be synthesized using a polymerase capable of incorporating a second modified nucleotide complementary to the first modified nucleotide of the extended capture probe. For example, TiTaq (a nuclease deficient, N-terminal truncated mutant of *Thermus aquaticus* DNA polymerase) is capable of incorporating isoCTP and isoGTP against template isoG and isoC respectively. Isoguanosine:isocytosine (isoG:isoC) base pair can be extended, replicated, and amplified.

Accordingly, in some embodiments extended capture probes have an incorporated isoG and complements of the extended capture probe have an incorporated isoC at the corresponding point of incorporation. In other embodiments, extended capture probes have an incorporated isoC and complements of the extended capture probe have an incorporated isoG at the corresponding point of incorporation. It will be appreciated that various concentrations of modified nucleotide can be used during capture probe extension in order to achieve a desired rate of incorporation.

In several embodiments, a sequencing read is initiated from the point of incorporation of the modified nucleotide into the extended capture probe. A sequencing primer can be hybridized to extended capture probes or their complements, which may be optionally amplified prior to initiating a sequence read, and extended in the presence of natural nucleotides. Extension of the sequencing primer will stall at the point of incorporation of the first modified nucleotide incorporated in the template, and a complementary modified nucleotide can be incorporated at the point of stall using a polymerase capable of incorporating a modified nucleotide (e.g. TiTaq polymerase). A sequencing read is initiated at the first base after the stall or point of modified nucleotide incorporation. In some embodiments, sequencing-by-synthesis initiates at the first base after the stall or point of modified nucleotide incorporation.

One of ordinary skill in the art will understand that the concentration of modified nucleotide during capture probe extension can be varied such that incorporations are relatively infrequent, which provides a plurality of extended capture probes having varying points of incorporation of modified nucleotide. Generating sequence information from a plurality of nucleotide templates having varying sequencing initiation in the above described manner provides a set of overlapping sequence reads. In several embodiments, these overlapping sequence reads are assembled into a contiguous nucleotide sequence of a nucleic acid of interest.

Arrays

Further embodiments of the methods and compositions described herein employ arrays. In some embodiments, an array refers to a substrate, such as a solid support, comprising a plurality of polynucleotides at distinguishable locations.

Some embodiments described herein relate to an array having a plurality of amplicon comprising amplified deletion products distributed on its surface at a site. In certain embodiments, the amplicons correspond to different deletion products of varying lengths less than the full length template.

Additional embodiments relate to an array having a plurality of amplicons that do not necessarily include amplified deletion products. Rather, the amplicons are distributed on surface of the array substrate at a site. In such embodiments, amplicons comprise polynucleotides that have a modified nucleotide incorporated at the same sequence location. The location of incorporation of the modified nucleotide is different for different amplicons.

In some embodiments of the arrays described herein, amplicons have an oligonucleotide tag complementary to a sequencing primer. The array can include a flow chamber and have a planar surface, patterned surface, or surface in a flow chamber or channel of a flow chamber. In some embodiments, the site on the surface of the array includes a well.

In some embodiments, the amplicons present on the array surface have an oligonucleotide tag. In some embodiments, the tag is complementary to a sequencing primer.

In some embodiments, the arrays can be within or otherwise include a flow chamber. In some embodiments, the arrays described herein can have a planar surface, a patterned surface, an irregular surface or an uneven surface. In some embodiments, the array substrate can include a surface in a flow chamber or a channel of a flow chamber. In some embodiments, the site on the surface of the array includes a well.

In preferred embodiments, the arrays described herein further comprise one or more sequencing enzymes associated with amplicons on the array. Exemplary sequencing enzymes include, but are not limited to, polymerases, ligases, nucleases as well as enzymes and systems of multiple enzymes that can produce a detectable signal, for example sulfurylase and luciferase.

Arrays can have one or more surfaces on which capture probes are distributed. In some embodiments, all of the capture probes distributed on an array surface are identical to each other. In other embodiments, some of the capture probes distributed on the array surface are identical to each other but different from one or more other capture probes distributed on the array surface. In still other embodiments, most or all of the capture probes distributed on an array surface are different from each other.

In embodiments where capture probes are distributed on an array surface, the capture probes can be distributed at sites. In some embodiments, a site is a feature having a plurality of copies of a particular capture probe. Thus, an array can comprise a plurality of sites or features. In some embodiments, a space separates each site from another such that the sites are noncontiguous. In other embodiments, the sites are contiguous. For some of the arrays described herein, sites can be present on the array surface at a density of greater than 10 sites per square millimeter. For other arrays, sites can be present on the array surface at a density of greater than 100 sites per square millimeter, greater than 1000 sites per square millimeter, greater than 10,000 sites per square millimeter, greater than 100,000 sites per square millimeter, greater than 1,000,000 sites per square millimeter, greater than 10,000,000 sites per square millimeter, greater than 100,000,000 sites per square millimeter or greater than 1,000,000,000 sites per square millimeter.

In some embodiments, polynucleotides are attached to a site on the surface of a substrate. In some embodiments, the site is a feature on the substrate having any size or dimension accommodating a plurality of polynucleotides within detectable limits of resolution. In other embodiments, the site is a feature on the substrate having any size or dimension accommodating a plurality of polynucleotides, wherein more than 2, more than 3, more than 4, more than 5, more than 6, more than 7, more than 8, more than 9, more than 10, more than 15, more than 20, more than 30, more than 40, more than 50, more than 75 or more than 100 polynucleotides of the plurality of polynucleotides comprises different sequencing initiation start points with respect to each other. For example, a sequencing initiation point can include, a modified nucleotide, a deletion end or other modified polynucleotide end, or a primer end hybridized to an adaptor that is ligated to a deletion end or other modified polynucleotide end. In such embodiments, the plurality of polynucleotides is attached at an area or site on the surface of the substrate such that polynucleotides having a different sequencing initiation point are separated from each other so as to form different zones, wherein each zone includes a polynucleotide having a different sequencing initiation point. Each of the different zones of the site comprises a plurality of polynucleotides having a same sequencing initiation point. As such, the site is variegated with respect to polynucleotide composition so as to have abutting zones, wherein polynucleotides in the same zone comprise the same sequence initiation start point, and wherein abutting zones comprise polynucleotides having a different sequence initiation start point. In such a manner, a detectable signal can be discretely produced and resolved at each zone, thereby avoiding the necessity of deconvoluting a combined signal that would be produced if the different polynucleotides were distributed at a site in a random or disorganized manner.

In some embodiments, a site is surrounded by a border. In some embodiments, the border is a physical structure. In some embodiments, the border is a virtual structure that is produced during the imaging of the array surface. A border that surrounds a site will typically not intervene between two or more zones of the site.

In some embodiments, a site includes less area than the area of an array surface where nucleic acids are attached. In certain embodiments, a site includes less than 90%, less than 80%, less than 70%, less than 60%, less than 50%, less than 40%, less than 30%, less than 20%, less than 10%, less than 5%, less than 4%, less than 3%, less than 2%, less than 1%, less than 0.5%, less than 0.1%, less than 0.01%, less than 0.001%, less than 0.0001%, or less than 0.00001% of the totality of the area of an array surface where nucleic acids are attached. In certain embodiments, a site includes less than 90%, less than 80%, less than 70%, less than 60%, less than 50%, less than 40%, less than 30%, less than 20%, less than 10%, less than 5%, less than 4%, less than 3%, less than 2%, less than 1%, less than 0.5%, less than 0.1%, less than 0.01%, less than 0.001%, less than 0.0001%, or less than 0.00001% of the totality of a demarcated area on an array substrate, whether physically or virtually demarcated, where nucleic acids are attached.

In some embodiments, a site includes the entire area of an array surface where nucleic acids are attached. In certain embodiments, a site includes 100% of the totality of a demarcated area on an array substrate, whether physically or virtually demarcated, where nucleic acids are attached. In various embodiments, a site includes the entire surface of an array (e.g. the entire surface of a substrate). In embodiments featuring deletion products derived from different nucleic acids of interest that include distinguishable oligonucleotide index tags, a site can include the entire surface of a substrate.

In various embodiments, a site is a feature in the micron range, which can accommodate a plurality of polynucleotides detectable and/or resolvable by current imaging devices such as scanners. In some embodiments, the site is a feature of about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4 s, 5, 6 square microns, 7, 8, 9, 10, 11, 12, 13, 14, 15, 20, 25, 30, 35, 40, 45, to about 50 square microns, or any size in between any of the foregoing values.

In other embodiments, a site is a feature in the sub-micron range that accommodates a plurality of polynucleotides detectable and/or resolvable by current imaging devices such as scanners. In some embodiments, the site is a feature size of about 1, 5, 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, or about 1000 square nanometers, or any size in between any of the foregoing values.

It will be understood that several embodiments contemplate a site that is a feature in the picometer range. Accordingly, in some embodiments, the site is a feature of about 1, 5, 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, or about 1000 square picometers, or any size in between any of the foregoing values.

In various embodiments, at least two polynucleotides are attached to a site. The embodiments of the present invention are not constrained to a particular maximum number of polynucleotides attached to a site. However, the maximum density of polynucleotides per unit area that can practically be resolved by an imaging device is a factor in the number of polynucleotides attached to a site.

In several embodiments, the plurality of polynucleotides attached to a site on the surface of a substrate have sequences that are overlapping nucleotide regions corresponding to a contiguous nucleotide sequence of a nucleic acid of interest. In various embodiments, the site to which these overlapping nucleotide regions are attached is a feature of any size described herein sufficient to accommodate the necessary number or density of overlapping nucleotide regions to obtain the contiguous nucleotide sequence of the nucleic acid of interest. For example, in several embodiments a feature includes at least one polynucleotide comprising the contiguous full length sequence of the target nucleic acid and a sufficient number of deletion products of varying lengths less than the full length sequence of the target nucleic acid, from which overlapping sequencing reads can be generated and assembled into the contiguous sequence of the target nucleic acid.

It will be appreciated that a person of ordinary skill in the art will select an appropriately sized site taking into account the length of the nucleic acid of interest, which bears on the number or density of overlapping nucleotide regions necessary to obtain the contiguous sequence of the nucleic acid of interest, and the limit of resolution of the detection or imaging device. In some embodiments, the site is the smallest feature required to obtain the contiguous sequence of a nucleic acid of interest from the overlapping nucleotide regions attached to the site. In some embodiments, the site is a larger feature size than required to obtain the contiguous sequence of a nucleic acid of interest from the overlapping nucleotide regions attached to the site.

The methods set forth herein can use arrays having features at any of a variety of densities including, for example, at least about 10 features/cm$^2$, 100 features/cm$^2$, 500 features/cm$^2$, 1,000 features/cm$^2$, 5,000 features/cm$^2$, 10,000 features/cm$^2$, 50,000 features/cm$^2$, 100,000 features/cm$^2$, 1,000,000 features/cm$^2$, 5,000,000 features/cm$^2$, or higher.

In some embodiments of the present invention, capture probes refer to molecules that are associated with an array that comprise one or more nucleic acids. In some embodiments, the capture probes can be nucleic acids that bind, hybridize or otherwise interact with one or more single-stranded nucleic acids that are transferred to the array. In preferred embodiments, the capture probes are oligonucleotides or otherwise comprise one or more oligonucleotides. In such embodiments, the capture probes comprise oligonucleotides that have an average length of 5 nucleotides, 6 nucleotides, 7 nucleotides, 8 nucleotides, 9 nucleotides, 10 nucleotides, 11 nucleotides, 12 nucleotides, 13 nucleotides, 14 nucleotides, 15 nucleotides, 16 nucleotides, 17 nucleotides, 18 nucleotides, 19 nucleotides, 20 nucleotides, 21 nucleotides, 22 nucleotides, 23 nucleotides, 24 nucleotides, 25 nucleotides, 26 nucleotides, 27 nucleotides, 28 nucleotides, 29 nucleotides, 30 nucleotides, 31 nucleotides, 32 nucleotides, 33 nucleotide, 34 nucleotides, 35 nucleotides, 36 nucleotides, 37 nucleotides, 38 nucleotides, 39 nucleotides, 40 nucleotides, 41 nucleotides, 42 nucleotides, 43 nucleotides, 44 nucleotides, 45 nucleotides, 46 nucleotides, 47 nucleotides, 48 nucleotides, 49 nucleotides, 50 nucleotides, 51 nucleotides, 52 nucleotides, 53 nucleotides, 54 nucleotides, 55 nucleotides, 56 nucleotides, 57 nucleotides, 58 nucleotides, 59 nucleotides, 60 nucleotides, 61 nucleotides, 62 nucleotides, 63 nucleotides, 64 nucleotides, 65 nucleotides, 66 nucleotides, 67 nucleotides, 68 nucleotides, 69 nucleotides, 70 nucleotides, 71 nucleotides, 72 nucleotides, 73 nucleotides, 74 nucleotides or 75 nucleotides. In other embodiments, oligonucleotides have an average length of greater than 75 nucleotides.

With respect to some of the arrays described herein, the capture probes are coupled to an array surface. Such coupling can be via a direct attachment of the capture probe to the array surface. Direct attachment can include, but is not limited to, covalent attachment, non-covalent attachment, and adsorptive attachment. Alternatively, capture probes can be attached to the array surface via one or more intermediate molecules or particles. A probe can be attached to an array surface via the 3' end of the probe or via the 5' end of the probe. The attachment can block or inhibit enzymatic degradation of the probe. For example, attachment of a probe to a surface via the 3' end can prevent degradation of the probe by exonuclease III. Attachment of a probe to a surface via the 5' end can prevent degradation of the probe by lambda exonuclease or T7 exonuclease. Exemplary attachments are described, for example, in US Patent Application Publication No. 2006/0127930 A1, which is incorporated herein by reference and also in references listed below in regard to various arrays.

Depending on the deposition method, the capture probes can be distributed on the array surface in either a random or ordered distribution. For example, in some embodiments, capture probes are synthesized directly on the array surface such that the position of each capture probe is known. In such embodiments, the capture probes can be synthesized in any order that is desired. For example, capture probes may be grouped by functionality or binding affinity for a particular molecule. In other embodiments, the capture probes are synthesized then coupled to an array surface. In such embodiments, the capture probes can be coupled to specific areas of the array surface such that the specific areas of the array surface comprise a defined set of capture probes.

With respect to other arrays described herein, capture probes are not attached directly to the array, but rather, they are associated with the array through intermediate structures, such as linkers or particles. In such embodiments, a plurality of particles is distributed on the array. The plurality of particles can comprise particles that have one or more capture probes coupled thereto, as well as particles that do not have any capture probes coupled thereto. In some embodiments, all particles of the plurality of particles have one or more identical capture probes coupled thereto. In certain embodiments, where pluralities of particles are used, the capture probes coupled the particles are identical to each other such that all particles have the same identical capture probes coupled thereto. In other embodiments, where pluralities of particles are used, some or all of the capture probes coupled to the particles are different from each other such that some particles have capture probes coupled thereto that are different from the capture probes attached to other particles. In preferred embodiments, the particles are inanimate, non-living beads or microspheres. In further embodiments, the microspheres can be porous. The particles can be substantially non-compressible and non-deformable, for example, under the conditions used for fluidic manipulations, amplification or sequencing.

In certain embodiments of the present invention, a plurality of particles is distributed on the surface of an array. In some embodiments, the particles are distributed on the array such that one or more particles end up in a depression present on the array. In some embodiments, the depressions are configured to hold a single particle. In other embodiments, the depressions are configured to hold thousands, or even millions, of particles.

The plurality of particles can be distributed on the array so that they are orderly or randomly distributed. In particular embodiments, an array can comprise particles carrying different functionalities that are distributed on an array comprising a patterned surface of sites, each capable of holding an individual particle. In some embodiments, one or more particles are present in wells of the array substrate.

Arrays described herein can have a variety of surfaces. In some embodiments, an array surface can comprise a fiber optic bundle. Arrays having planar surfaces or surfaces with one or more depressions, channels or grooves are particularly useful. In addition, some of the arrays have a non-porous surface. In some embodiments, the entire array is non-porous. In other embodiments, the array has at least one porous or semi-porous surface but is primarily non-nonporous.

Preferred materials for array substrates include, but are not limited to glass, silicon, plastic or non-reactive polymers. Arrays described herein can be rigid or flexible. In some embodiments, the array is rigid, whereas in other embodiments, the array is not rigid but comprises at least one rigid surface. Other arrays contemplated herein can comprise a flexible array substrate having a flexible support, such as that described in U.S. patent application Ser. No. 10/285,759, now U.S. Pat. No. 7,422,911, the disclosures of which are hereby incorporated expressly by reference in their entireties.

Some of the arrays described herein include one or more patterned surfaces. In such embodiments, the patterned surface may comprise depressions, such as wells, grooves, channels or indentations. Depressions can be sized so as to accommodate as few as one particle or as many as several million particles.

In further embodiments an array can comprise a composite array (array of subarrays) as described in U.S. Pat. Nos. 6,429,027 or 5,545,531, the disclosures of which are hereby incorporated expressly by reference in their entirety. Composite arrays can comprise a plurality of individual arrays on a surface of the array or distributed in depressions present on the array surface. The plurality of individual arrays on a surface of the array or distributed in depressions present on the array surface can be referred to as subarrays. For example, in a composite array, a single subarray can be present in each of a plurality of depressions present on the array. In other embodiments, multiple subarrays can be present in each depression of a plurality of depressions present on the array. Individual subarrays can be different from each other or can be the same or similar to other subarrays present on the array. Accordingly, in some embodiments, the surface of a composite array can comprise a plurality of different and/or a plurality of identical, or substantially identical, subarrays. Moreover, in some embodiments, the surface of an array comprising a plurality of subarrays can further comprise an inter-subarray surface. By "inter-subarray surface" or "inter-subarray spacing" is meant the portion of the surface of the array not occupied by subarrays. In some embodiments, "inter-subarray surface" refers to the area of array surface between a first subarray and an adjacent second subarray.

Subarrays can include some or all of the features of the arrays described herein. For example, subarrays can include depressions that are configured to contain one or more particles. Moreover, subarrays can further comprise their own subarrays.

Exemplary arrays that can be utilized in combination with the methods and compositions described herein include, without limitation, those in which beads are associated with a solid support, examples of which are described in U.S. Pat. Nos. 6,355,431; 6,327,410; 6,770,441; US Published Patent Application No. 2004/0185483; US Published Patent Application No. 2002/0102578 and PCT Publication No. WO 00/63437, each of which is incorporated herein by reference in its entirety. Beads can be located at locations, such as wells, on a solid-phase support, whereby each location accommodates a single bead.

Any of a variety of other arrays known in the art or methods for fabricating such arrays can be used. Commercially available microarrays that can be used include, for example, an Affymetrix® GeneChip® microarray or other microarray synthesized in accordance with techniques sometimes referred to as VLSIPS™ (Very Large Scale Immobilized Polymer Synthesis) technologies as described, for example, in U.S. Pat. Nos. 5,324,633; 5,744,305; 5,451, 683; 5,482,867; 5,491,074; 5,624,711; 5,795,716; 5,831, 070; 5,856,101; 5,858,659; 5,874,219; 5,968,740; 5,974, 164; 5,981,185; 5,981,956; 6,025,601; 6,033,860; 6,090, 555; 6,136,269; 6,022,963; 6,083,697; 6,291,183; 6,309, 831; 6,416,949; 6,428,752 and 6,482,591, each of which is hereby incorporated by reference in its entirety. A spotted microarray can also be used in a method of the invention. An exemplary spotted microarray is a CodeLink™ Array available from Amersham Biosciences. Another microarray that is useful in the invention is one that is manufactured using inkjet printing methods such as SurePrint™ Technology available from Agilent Technologies.

Preparation of Amplified Polynucleotides and Deletion Products

In some embodiments of the methods described herein, an amplification step is performed. In some embodiments, target nucleic acids may be amplified prior to providing them to the array. In other embodiments, polynucleotides, such as template nucleic acids, attached to the array, for example by hybridization with a capture probe, can be amplified prior to processing the polynucleotides to produce a set of overlapping regions to be sequenced. Additionally or alternatively, amplification may occur subsequent to processing the polynucleotides to produce a set of overlapping regions to be sequenced.

In a particular embodiment, clustered arrays of nucleic acid colonies can be prepared as described in U.S. Pat. No. 7,115,400; US Published Patent Application No. 2005/ 0100900 A1; PCT Publication No. WO 00/18957 or PCT Publication No. WO 98/44151, the contents of which are herein incorporated by reference in their entireties. Such methods are known as bridge amplification or solid-phase amplification and are particularly useful for sequencing applications. In some embodiments, a target nucleic acid or deletion product can be amplified for use with the methods described herein. Such embodiments include preparing amplified libraries of target nucleic acids. Library preparation can be accomplished by random fragmentation of DNA, followed by in vitro ligation of common adaptor sequences.

Various protocols can be used to generate an array of millions of spatially immobilized PCR colonies, sometimes referred to as polonies, on a substrate. For example, such clonally clustered amplicons of target nucleic acids can be generated by in situ polonies, emulsion PCR, or bridge PCR (Mitra, R. D. & Church, G. M. "In situ localized amplification and contact replication of many individual DNA molecules." *Nucleic Acids Res.* 27, e34 (1999); Dressman, D., Yan, H., Traverso, G., Kinzler, K. W. & Vogelstein, B. "Transforming single DNA molecules into fluorescent magnetic particles for detection and enumeration of genetic variations." *Proc. Natl. Acad. Sci. USA* 100, 8817-8822 (2003); Adessi, C. et al. "Solid phase DNA amplification: characterization of primer attachment and amplification mechanisms." *Nucleic Acids Res.* 28, e87 (2000); Fedurco, M., Romieu, A., Williams, S., Lawrence, I. & Turcatti, G. "BTA, a novel reagent for DNA attachment on glass and efficient generation of solid-phase amplified DNA colonies." *Nucleic Acids Res.* 34, e22 (2006), each of which is incorporated by reference herein in their entireties).

In embodiments using emulsion PCR, an in vitro-constructed adaptor flanked shotgun library can be PCR amplified in a water-in-oil emulsion. The PCR is multi-template PCR, because only a single primer pair is used. One of the PCR primers is tethered to the surface (5'-attached) of micron-scale beads that are also included in the reaction. A low template concentration results in most bead-containing compartments having either zero or one template molecule present. In productive emulsion compartments (where both a bead and template molecule is present), PCR amplicons can be captured to the surface of the bead. After breaking the emulsion, beads bearing amplification products can be selectively enriched. Each clonally amplified bead will bear on its surface PCR products corresponding to amplification of a single molecule from the template library. Various embodiments of emulsion PCR methods that are useful are set forth in U.S. Patent Application Publication No. 2005/0042648; U.S. Patent Application Publication No. 2005/0079510; U.S.

Patent Application Publication No. 2005/0130173 and WO 05/010145, each of which is incorporated herein by reference.

In some embodiments, clustered amplicons that can serve as sequencing features are generated by emulsion PCR on a surface of a substrate. In some embodiments, clustered amplicons are attached to the surface of a bead, preferably micron-scale or sub-micron-scale beads adapted to be immobilized to a planar substrate for sequencing. In other embodiments, amplicon-bearing beads can be placed into wells of an array. For example, microfabricated arrays can be designed to have picoliter-sized wells that accommodate a single bead per well. Features attached to beads can be sequenced by any method, including but not limited to sequencing-by-synthesis (driven by DNA polymerase or DNA ligase), pyrosequencing, and sequencing by hybridization. In some embodiments, amplification methods other than emulsion PCR can be used to produce amplicons.

In embodiments using bridge PCR, also known as cluster PCR, an in vitro-constructed adaptor-flanked shotgun library can be PCR amplified using primers coated densely on the surface of a substrate. The primers are attached at their 5' ends by a flexible linker. Amplification products originating from any given member of the template library remain locally tethered near the point of origin. At the conclusion of the PCR, each clonal cluster contains ~1,000 copies of a single member of the template library. Accurate measurement of the concentration of the template library can be used to optimize the cluster density while simultaneously avoiding overcrowding. Various embodiments of bridge PCR methods that are useful are set forth in U.S. Patent Application Publication No. 2007/0128624, WO 07/010251, U.S. Pat. Nos. 6,090,592 and 5,641,658, each of which is incorporated herein by reference. Generally, in bridge amplification (e.g. bridge PCR), also known as cluster amplification, both forward and reverse primers are attached to a substrate typically at their 5' ends by a flexible linker. Amplicons originating from a template library or template of interest remain attached to the substrate and clustered at a site on the substrate. Thus, bridge PCR amplifies clonal sequencing features. A plurality of clusters can be amplified to sites on a flow-cell. Amplicons are linearized to single strands and a sequencing primer is hybridized to a universal sequence flanking the nucleotide region of interest. Sequencing can be performed by any methodology described herein, preferably by sequencing-by-synthesis (SBS) involving reversible terminator nucleotides having a cleavable moiety at the 3' end and a cleavable fluorescent label.

Such embodiments, can generate PCR amplicons derived from library molecules at sites or features on a planar substrate (in situ polonies, bridge PCR), or to the surface of micron-scale beads, which can be recovered and arrayed (emulsion PCR).

Nucleic Acid Sequencing

Embodiments of the methods and compositions disclosed herein relate to nucleic acid (polynucleotide) sequencing. In some methods and compositions described herein, the nucleotide sequence of a portion of a target nucleic acid or fragment thereof can be determined using a variety of methods and devices. Examples of sequencing methods include electrophoretic, sequencing by synthesis, sequencing by ligation, sequencing by hybridization, single-molecule sequencing, and real time sequencing methods. In some embodiments, the process to determine the nucleotide sequence of a target nucleic acid or fragment thereof can be an automated process. In some embodiments, capture probes can function as primers permitting the priming of a nucleotide synthesis reaction using a polynucleotide from the nucleic acid sample as a template. In this way, information regarding the sequence of the polynucleotides supplied to the array can be obtained. In some embodiments, polynucleotides hybridized to capture probes on the array can serve as sequencing templates if primers that hybridize to the polynucleotides bound to the capture probes and sequencing reagents are further supplied to the array. Methods of sequencing using arrays have been described previously in the art.

Electrophoretic sequencing methods include Sanger sequencing protocols and conventional electrophoretic techniques (Sanger, F., Nicklen, S. and Coulson, A. R. (1977) DNA sequencing with chain-terminating inhibitors. Proc. Natl. Acad. Sci. USA. 74(12), 5463-7; Swerdlow, H., Wu, S. L., Harke, H. & Dovichi, N.J. Capillary gel electrophoresis for DNA sequencing. Laser-induced fluorescence detection with the sheath flow cuvette. J. Chromatogr. 516, 61-67 (1990); Hunkapiller, T., Kaiser, R. J., Koop, B. F. & Hood, L. Large-scale and automated DNA sequence determination. Science 254, 59-67 (1991)). In such embodiments, electrophoresis can be carried out on a microfabricated device (Paegel, B. M., Blazej, R. G. & Mathies, R. A. Microfluidic devices for DNA sequencing: sample preparation and electrophoretic analysis. Curr. Opin. Biotechnol. 14, 42-50 (2003); Hong, J. W. & Quake, S. R. Integrated nanoliter systems. Nat. Biotechnol. 21, 1179-1183 (2003), the disclosures of which are incorporated herein by reference in their entireties).

As described above, one or more sequencing steps can be performed subsequent to attachment and/or processing steps. Sequencing can be carried out on the solid-phase surface to which colonies are attached. Typical sequencing steps can include, but are not limited to, one or more of those used in sequencing-by-synthesis (SBS). In SBS, four fluorescently labeled modified nucleotides are used to determine the sequence of nucleotides for nucleic acids present on the surface of a support structure such as a flowcell. Exemplary SBS systems and methods which can be utilized with the apparatus and methods set forth herein are described in US Patent Application Publication No. 2007/0166705, US Patent Application Publication No. 2006/0188901, U.S. Pat. No. 7,057,026 US Patent Application Publication No. 2006/0240439, US Patent Application Publication No. 2006/0281109, PCT Publication No. WO 05/065814, US Patent Application Publication No. 2005/0100900, PCT Publication No. WO 06/064199 and PCT Publication No. WO 07/010251, each of which is incorporated herein by reference in its entirety.

With respect to other uses of the methods and compositions described herein, arrayed nucleic acids are treated by several repeated cycles of an overall sequencing process. In some embodiments, the attached nucleic acids are prepared such that they include an oligonucleotide primer (capture probe) hybridized to an unknown target sequence or hybridized to another template nucleic acid or polynucleotide whether the sequence identity is known or unknown. To initiate the first SBS sequencing cycle, one or more differently labeled nucleotides and a DNA polymerase can be introduced to the array. Either a single nucleotide can be added at a time, or the nucleotides used in the sequencing procedure can be specially designed to possess a reversible termination property, thus allowing each cycle of the sequencing reaction to occur simultaneously in the presence of all four labeled nucleotides (A, C, T, G). Following nucleotide addition, signals produced at the features on the surface can be detected to determine the identity of the incorporated nucleotide (based on the labels on the nucleotides). Reagents can then be added to remove the blocked 3' terminus (if appropriate) and to remove labels from each incorporated base. Reagents, enzymes and other substances can be removed between steps by washing. Such cycles are then repeated and the sequence of each cluster is read over the multiple chemistry cycles.

As set forth above, SBS techniques generally involve the enzymatic extension of a nascent nucleic acid strand through the iterative addition of nucleotides against a template strand. Each nucleotide addition queries one or a few bases of the template strand. In one exemplary type of SBS, cycle sequencing is accomplished by stepwise addition of reversible terminator nucleotides containing, for example, a cleavable or photobleachable dye label. This approach is being commercialized by Solexa (now Illumina), and is also described in WO 91/06678, which is incorporated herein by reference in its entirety. The availability of fluorescently-labeled terminators in which both the termination can be reversed and the fluorescent label cleaved is important to facilitating efficient cyclic reversible termination (CRT) sequencing. Polymerases can also be co-engineered to efficiently incorporate and extend from these modified nucleotides. In particular embodiments, reversible terminators/cleavable fluors can include fluor linked to the ribose moiety via a 3' ester linkage (Metzker, Genome Res. 15:1767-1776 (2005), which is incorporated herein by reference). Other approaches have separated the terminator chemistry from the cleavage of the fluorescence label (Ruparel et al., Proc Natl Acad Sci USA 102: 5932-7 (2005), which is incorporated herein by reference in its entirety). Ruparel et al described the development of reversible terminators that used a small 3' allyl group to block extension, but could easily be deblocked by a short treatment with a palladium catalyst. The fluorophore was attached to the base via a photocleavable linker that could easily be cleaved by a 30 second exposure to long wavelength UV light. Thus, either disulfide reduction or photocleavage can be used to cleave a linker. Another approach to reversible termination is the use of natural termination that ensues after placement of a bulky dye on a dNTP. The presence of a charged bulky dye on the dNTP can act as an effective terminator through steric and/or electrostatic hindrance. The presence of one incorporation event prevents further incorporations unless the dye is removed. Cleavage of the dye removes the fluor and effectively reverses the termination. Examples of modified nucleotides are also described in U.S. Pat. Nos. 7,427,673, and 7,057,026, the disclosures of which are incorporated herein by reference in their entireties.

In certain preferred embodiments, sequencing is performed by sequencing-by-synthesis (SBS), in which one or more nucleotides or oligonucleotides are sequentially added to an extending polynucleotide chain in the 5' to 3' direction to form an extended polynucleotide complementary to the template nucleic acid to be sequenced. The identity of the base present in one or more of the added nucleotide(s) can be determined in a detection or imaging step, preferably after each nucleotide incorporation. In various embodiments involving SBS, fluorescently labeled nucleotides are used in the sequencing reaction. The four different bases are each labeled with a unique fluorescent label to permit identification of the incorporated nucleotide as successive nucleotides are added. The labeled nucleoside triphosphates also can have a removable 3' blocking group to prevent further incorporation. The label of the incorporated base can be determined and the blocking group removed to permit further extension.

The labels may be the same for each type of nucleotide, or each nucleotide type may carry a different label. This facilitates the identification of incorporation of a particular nucleotide. Thus, for example modified adenine, guanine, cytosine and thymine would all have attached a different fluorophore to allow them to be discriminated from one another readily. When sequencing on arrays, a mixture of labeled and unlabelled nucleotides may be used. Detectable labels such as fluorophores can be linked to nucleotides via the base using a suitable linker. The linker may be acid labile, photolabile or contain a disulfide linkage. Preferred labels and linkages include those disclosed in U.S. Pat. No. 7,057,026. Other linkages, in particular phosphine-cleavable azide-containing linkers, may be employed in the invention as described in greater detail in US 2006/0160081. The contents of U.S. Pat. No. 7,057,026 and US 2006/0160081 are incorporated herein by reference.

Methods for detecting fluorescently labeled nucleotides generally use incident light (e.g. laser light) of a wavelength specific for the fluorescent label, or the use of other suitable sources of illumination, to excite the fluorophore. Fluorescent light emitted from the fluorophore may then be detected at the appropriate wavelength using a suitable detection system such as for example a Charge-Coupled-Device (CCD) camera, which can optionally be coupled to a magnifying device, a fluorescent imager or a confocal microscope. In embodiments involving sequencing carried out on an array, detection of an incorporated base may be performed by using a scanning microscope to scan the surface of the array with a laser and image fluorescent labels attached to the incorporated nucleotide(s). A sensitive 2-D detector, such as a charge-coupled detector (CCD), can be used to visualize the signals generated.

Other sequencing methods that use cyclic reactions can be used, such as those wherein each cycle can include steps of delivering one or more reagents to nucleic acids, for example, pyrosequencing and sequencing-by-ligation. Useful pyrosequencing reactions are described, for example, in US Patent Application Publication No. 2005/0191698 and U.S. Pat. No. 7,244,559, each of which is incorporated herein by reference. Sequencing-by-ligation reactions are described, for example, in Shendure et al. *Science* 309:1728-1732 (2005); U.S. Pat. Nos. 5,599,675; and 5,750,341, each of which is incorporated herein by reference in its entirety.

Several embodiments include pyrosequencing techniques. Pyrosequencing detects the release of inorganic pyrophosphate (PPi) as particular nucleotides are incorporated into the nascent strand (Ronaghi, M., Karamohamed, S., Pettersson, B., Uhlen, M. and Nyren, P. (1996) "Real-time DNA sequencing using detection of pyrophosphate release." *Analytical Biochemistry* 242(1), 84-9; Ronaghi, M. (2001) "Pyro sequencing sheds light on DNA sequencing." *Genome Res.* 11(1), 3-11; Ronaghi, M., Uhlen, M. and Nyren, P. (1998) "A sequencing method based on real-time pyrophosphate." *Science* 281(5375), 363; U.S. Pat. Nos. 6,210,891; 6,258, 568 and 6,274,320, the disclosures of which are incorporated herein by reference in their entireties). In pyrosequencing, released PPi can be detected by being immediately converted to adenosine triphosphate (ATP) by ATP sulfurylase, and the level of ATP generated is detected via luciferase-produced photons.

Some embodiments include methods utilizing sequencing by hybridization techniques. In such embodiments, differential hybridization of oligonucleotide probes can be used to decode a target DNA sequence (Bains, W. and Smith, G. C. A novel method for nucleic acid sequence determination. Journal of Theoretical Biology 135(3), 303-7 (1988);

Drmanac, S. et al., Accurate sequencing by hybridization for DNA diagnostics and individual genomics. Nature Biotechnology 16, 54-58 (1998); Fodor, S. P. A., Read, J. L., Pirrung, M. C., Stryer, L., Lu, A. T. and Solas, D. Light-directed, spatially addressable parallel chemical synthesis. Science 251(4995), 767-773 (1995); Southern, E. M. (1989) Analyzing polynucleotide sequences. WO 1989/10977), the disclosures of which are incorporated herein by reference in their entireties). The target DNA can be immobilized on a solid support and serial hybridizations can be performed with short probe oligonucleotides, for example, oligonucleotides 5 to 8 nucleotides in length. The extent to which specific probes bind to the target DNA can be used to infer the unknown sequence. Target DNA can also be hybridized to high density oligonucleotide arrays (Lipshutz, R. J. et al., (1995) Using oligonucleotide probe arrays to access genetic diversity. Biotechniques 19, 442-447, the disclosure of which is incorporated herein by reference in its entirety).

Some embodiments can utilize nanopore sequencing (Deamer and Akeson, 2000; Deamer and Branton, 2002; Li et al., 2003, the disclosure of which is incorporated herein by reference in its entirety). In such embodiments, the target nucleic acid passes through a nanopore. The nanopore can be a synthetic pore or biological membrane protein, such as α-hemolysin (Deamer, D. W. & Akeson, M. Nanopores and nucleic acids: prospects for ultrarapid sequencing. Trends Biotechnol. 18, 147-151 (2000), the disclosure of which is incorporated herein by reference in its entirety). As the target nucleic acid passes through the nanopore, each base-pairs can be identified by measuring fluctuations in the electrical conductance of the pore. (U.S. Pat. No. 7,001,792; Soni, G. V. & Meller, A. Progress toward ultrafast DNA sequencing using solid-state nanopores. Clin. Chem. 53, 1996-2001 (2007); Healy, K. Nanopore-based single-molecule DNA analysis. Nanomed. 2, 459-481 (2007); Cockroft, S. L., Chu, J., Amorin, M. & Ghadiri, M. R. A single-molecule nanopore device detects DNA polymerase activity with single-nucleotide resolution. J. Am. Chem. Soc. 130, 818-820 (2008); Levene, M. J. et al. Zero-mode waveguides for single-molecule analysis at high concentrations. Science 299, 682-686 (2003), the disclosures of which are incorporated herein by reference in their entireties).

Some embodiments can utilize methods involving the real-time monitoring of DNA polymerase activity. Nucleotide incorporations can be detected through fluorescence resonance energy transfer (FRET) interactions between a fluorophore-bearing polymerase and γ-phosphate-labeled nucleotides, or with zeromode waveguides. The illumination can be restricted to a zeptoliter-scale volume around a surface-tethered polymerase such that incorporation of fluorescently labeled nucleotides can be observed with low background (Levene, M. J. et al. Zero-mode waveguides for single-molecule analysis at high concentrations. Science 299, 682-686 (2003); Lundquist, P. M. et al. Parallel confocal detection of single molecules in real time. Opt. Lett. 33, 1026-1028 (2008); Korlach, J. et al. Selective aluminum passivation for targeted immobilization of single DNA polymerase molecules in zero-mode waveguide nanostructures. Proc. Natl. Acad. Sci. USA 105, 1176-1181 (2008), the disclosures of which are incorporated herein by reference in their entireties).

The above SBS methods can be advantageously carried out in multiplex formats such that multiple different target nucleic acids are manipulated simultaneously. In particular embodiments, different target nucleic acids can be treated in a common reaction vessel or on a surface of a particular substrate. This allows convenient delivery of sequencing reagents, removal of unreacted reagents and detection of incorporation events in a multiplex manner. In embodiments using surface-bound target nucleic acids, the target nucleic acids can be in any of a variety of array formats. Several exemplary formats are set forth previously herein. In an array format, the target nucleic acids can be typically bound to a surface in a spatially distinguishable manner. The target nucleic acids can be bound by direct covalent attachment, attachment to a bead or other particle or binding to a polymerase or other molecule that is attached to the surface. The array can include a single copy of a target nucleic acid at each site (also referred to as a feature) or multiple copies having the same sequence can be present at each site or feature. Multiple copies can be produced by amplification methods such as, bridge amplification or emulsion PCR as described in further detail below.

In embodiments involving sequencing on a substrate such as an array, paired end reads may be obtained on nucleic acid clusters. Methods for obtaining paired end reads are described in WO/07010252 and WO/07091077, each of which is incorporated herein by reference. Paired end sequencing facilitates reading both the forward and reverse template strands of each cluster during one paired-end read. Generally, template clusters are amplified on the surface of a substrate (e.g. a flow-cell) by bridge amplification and sequenced by paired primers sequentially. Upon amplification of the template strands, a bridged double stranded structure is produced. This can be treated to release a portion of one of the strands of each duplex from the surface. The single stranded nucleic acid is available for sequencing, primer hybridization and cycles of primer extension. After the first sequencing run, the ends of the first single stranded template can be hybridized to the immobilized primers remaining from the initial cluster amplification procedure. The immobilized primers can be extended using the hybridized first single strand as a template to resynthesize the original double stranded structure. The double stranded structure can be treated to remove at least a portion of the first template strand to leave the resynthesized strand immobilized in single stranded form. The resynthesized strand can be sequenced to determine a second read, whose location originates from the opposite end of the original template fragment obtained from the fragmentation process.

It will be appreciated that any of the above-described sequencing processes can be incorporated into the methods and/or compositions described herein. Furthermore, it will be appreciated that other known sequencing processes can be easily by implemented for use with the methods and/or compositions described herein.

Sequence Assembly

Several embodiments described herein relate to methods of generating overlapping sequence reads and assembling them into a contiguous nucleotide sequence of a nucleic acid of interest. Assembly algorithms can align and merge overlapping sequence reads generated by methods of several embodiments herein to provide a contiguous sequence of a nucleic acid of interest. A person of ordinary skill in the art will understand which sequence assembly algorithms or sequence assemblers are suitable for a particular purpose taking into account the type and complexity of the nucleic acid of interest to be sequenced (e.g. genomic, PCR product, plasmid, BAC, EST, etc.), the number and/or length of deletion products or other overlapping regions generated, the type of sequencing methodology performed, the read lengths generated, whether assembly is de novo assembly of a previously unknown sequence or mapping assembly against a backbone sequence, etc. Furthermore, an appropriate data analysis tool will be selected based on the function desired, such as alignment of sequence reads, base-calling and/or polymorphism detection, de novo assembly, assembly from paired or unpaired reads, and genome browsing and annotation.

In several embodiments, overlapping sequence reads can be assembled by sequence assemblers, including but not limited to ABySS, AMOS, Arachne WGA, CAP3, PCAP, Celera WGA Assembler/CABOG, CLC Genomics Workbench, CodonCode Aligner, Euler, Euler-sr, Forge, Geneious, MIRA, miraEST, NextGENe, Newbler, Phrap, TIGR Assembler, Sequencher, SeqMan NGen, SHARCGS, SSAKE, Staden gap4 package, VCAKE, Phusion assembler, Quality Value Guided SRA (QSRA), Velvet (algorithm), and the like.

It will be understood that overlapping sequence reads can also be assembled into contigs or the full contiguous sequence of the nucleic acid of interest by available means of sequence alignment, computationally or manually, whether by pairwise alignment or multiple sequence alignment of overlapping sequence reads.

Algorithms suited for short-read sequence data may be used in a variety of embodiments, including but not limited to Cross_match, ELAND, Exonerate, MAQ, Mosaik, RMAP, SHRiMP, SOAP, SSAHA2, SXOligoSearch, ALLPATHS, Edena, Euler-SR, SHARCGS, SHRAP, SSAKE, VCAKE, Velvet, PyroBayes, PbShort, and ssahaSNP.

EXAMPLES

Having generally described embodiments of the present invention, a further understanding can be obtained by reference to certain specific examples which are provided herein for purposes of illustration only, and are not intended to be limiting.

Example 1

A duplex P5 adaptor is ligated to one end of a duplex target nucleic acid of interest and amplified. Amplified P5-target duplexes are denatured to single-stranded templates and hybridized to array-attached capture probes complementary to the P5 adaptor sequence. Capture probes are extended with polymerase in the presence of limiting amounts of terminator nucleotides, generating deletion products (i.e. extended to lengths that are less than the full length of the templates) (FIG. 1). Terminator nucleotides are deblocked, templates are dehybridized and P7 ssDNA adaptors are ligated with T4 ligase to the free ends of the deletion products. P7-deletion product strands are bridge amplified on the array via P7 complementary capture probes attached to the array, and sequenced from the non-attached free end by sequencing-by-synthesis to generate a set of overlapping sequencing reads. The overlapping sequencing reads are assembled to obtain a contiguous nucleotide sequence of the target nucleic acid.

Example 2

A duplex P5 adaptor is ligated to both ends of a duplex target nucleic acid of interest and amplified. Amplified P5-target duplexes are denatured to single-stranded templates and hybridized to array-attached capture probes complementary to the P5 adaptor sequence. Capture probes are extended with polymerase in the presence of limiting amounts of terminator nucleotides, generating deletion products (i.e. extended to lengths that are less than the full length of the templates) from both ends of the target nucleic acid. Terminator nucleotides are deblocked, templates are dehybridized and P7 ssDNA adaptors are ligated with T4 ligase to the free ends of the deletion products. P7-deletion product strands are bridge amplified on the array via P7 complementary capture probes attached to the array, and sequenced from the non-attached free end by sequencing-by-synthesis to generate a set of overlapping sequencing reads. The overlapping sequencing reads are assembled to obtain a contiguous nucleotide sequence of the target nucleic acid.

Example 3

A duplex P5 adaptor is ligated to one end of a duplex target nucleic acid of interest and amplified. Amplified P5-target duplexes are denatured to single-stranded templates and hybridized to array-attached capture probes complementary to the P5 adaptor sequence. Capture probes are fully extended with polymerase in the presence of natural nucleoside triphosphates. Extended capture probes are then digested with exonuclease (e.g. exo III) or endonuclease (e.g. DNase I), yielding deletion products having lengths less than the full length of the templates. Digestion is stopped, templates are dehybridized, and P7 ssDNA adaptors are ligated with T4 ligase to the free ends of the deletion products. P7-deletion product strands are bridge amplified on the array via P7 complementary capture probes attached to the array, and sequenced from the non-attached free end by sequencing-by-synthesis to generate a set of overlapping sequencing reads. The overlapping sequencing reads are assembled to obtain a contiguous nucleotide sequence of the target nucleic acid.

Example 4

A duplex P5 adaptor is ligated to one end of a duplex target nucleic acid of interest and amplified. Amplified P5-target duplexes are physically sheared by sonication, generating deletion products having lengths less than the full length of the insert. Deletion products are denatured to single-stranded templates and hybridized to array-attached capture probes complementary to the P5 adaptor sequence. Capture probes are extended with polymerase in the presence of natural nucleoside triphosphates. Templates are dehybridized and P7 ssDNA adaptors are ligated with T4 ligase to the free ends of the extended capture probes, which are bridge amplified on the array via P7 complementary capture probes attached to the array, and sequenced from the non-attached free end by sequencing-by-synthesis to generate a set of overlapping sequencing reads. The overlapping sequencing reads are assembled to obtain a contiguous nucleotide sequence of the target nucleic acid.

Example 5

A duplex P5 adaptor is ligated to one end of a duplex target nucleic acid of interest and amplified. Amplified P5-target duplexes are denatured to single-stranded templates and hybridized to array-attached capture probes complementary to the P5 adaptor sequence. Capture probes are fully extended with polymerase in the presence of natural nucleoside triphosphates. Extended capture probes are then physically sheared by sonication, generating deletion products (i.e. extended to lengths that are less than the full length of the templates). Templates are dehybridized and P7 ssDNA adaptors are ligated with T4 ligase to the free ends of the deletion products. P7-deletion product strands are bridge amplified on the array via P7 complementary capture probes attached to the array, and sequenced from the non-attached free end by sequencing-by-synthesis to generate a set of overlapping sequencing reads. The overlapping sequencing reads are assembled to obtain a contiguous nucleotide sequence of the target nucleic acid.

Example 6

A duplex P5 adaptor is ligated to one end of a duplex target nucleic acid of interest and amplified. Amplified P5-target duplexes are denatured to single-stranded templates and hybridized to array-attached capture probes complementary to the P5 adaptor sequence. Capture probes are fully extended with polymerase in the presence of natural nucleoside triphosphates. Extended capture probes are then nicked with DNase I, generating deletion products of different lengths. Optionally the nicked probes can be partially translated with DNA pol I, generating deletion products (i.e. translated to lengths that are less than the full length of the templates). Whether or not the optional translation step is carried out, templates are dehybridized and P7 ssDNA adaptors are ligated with T4 ligase to the free ends of the deletion products. P7-deletion product strands are bridge amplified on the array via P7 complementary capture probes attached to the array, and sequenced from the non-attached free end by sequencing-by-synthesis to generate a set of overlapping sequencing reads. The overlapping sequencing reads are assembled to obtain a contiguous nucleotide sequence of the target nucleic acid.

Example 7

Figure 2:
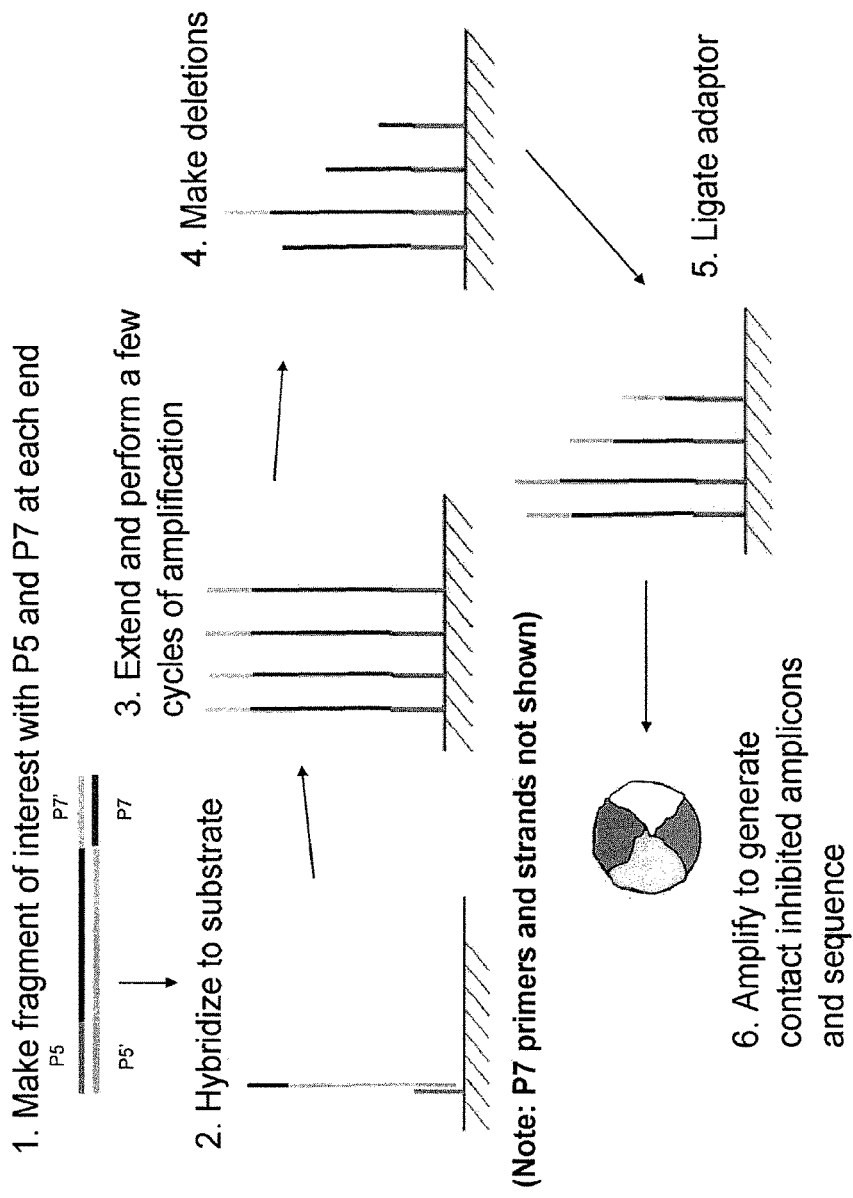
FIG. 2 is a schematic illustration showing a method of generating overlapping sequence reads and obtaining a contiguous nucleotide sequence of a nucleic acid of interest from deletion products having the same adaptor as attached to the full-length template.

As in FIG. 2, a duplex P5 adaptor is ligated to one end and a duplex P7 adaptor is ligated to the other end of a duplex target nucleic acid of interest and amplified. Amplified P5-target-P7 or P7-target-P5 duplexes are denatured to single-stranded templates and hybridized to array-attached capture probes complementary to the P5 and P7 adaptor sequence. Capture probes are fully extended with polymerase in the presence of natural nucleoside triphosphates and amplified by a few cycles of bridge amplification. Amplicons are then digested with exonuclease (e.g. exo III) or endonuclease (e.g. DNase I), yielding deletion products having lengths less than the full length of the polynucleotide templates. Digestion is stopped, templates are dehybridized, and P5 or P7 ssDNA adaptors are ligated with T4 ligase to the free ends of the deletion products. Adaptor-deletion product-adaptor strands are bridge amplified on the array via adaptor-complementary capture probes attached to the array, and sequenced from the non-attached free end by sequencing-by-synthesis to generate a set of overlapping sequencing reads. The overlapping sequencing reads are assembled to obtain a contiguous nucleotide sequence of the target nucleic acid.

A modified version of the method shown in FIG. 2 can be carried out wherein duplex P5 adaptor is initially ligated to both ends of the fragment in step 1. The resulting ligation product is amplified using primers that hybridize to priming sites present in the P5. Amplified P5-target-P5 duplexes are denatured to single-stranded templates and hybridized to array-attached capture probes complementary to the P5 adaptor sequence. Capture probes are fully extended with polymerase in the presence of natural nucleoside triphosphates and amplified by a few cycles of bridge amplification. Amplicons are then digested with exonuclease (e.g. exo III) or endonuclease (e.g. DNase I), yielding deletion products having lengths less than the full length of the polynucleotide templates. Digestion is stopped, templates are dehybridized, P7 ssDNA adaptors are ligated with T4 ligase to the free ends of the deletion products. Adaptor-deletion product-adaptor strands are bridge amplified on the array via adaptor-complementary capture probes attached to the array, and sequenced from the non-attached free end by sequencing-by-synthesis to generate a set of overlapping sequencing reads. The overlapping sequencing reads are assembled to obtain a contiguous nucleotide sequence of the target nucleic acid.

Example 8

Figure 3:
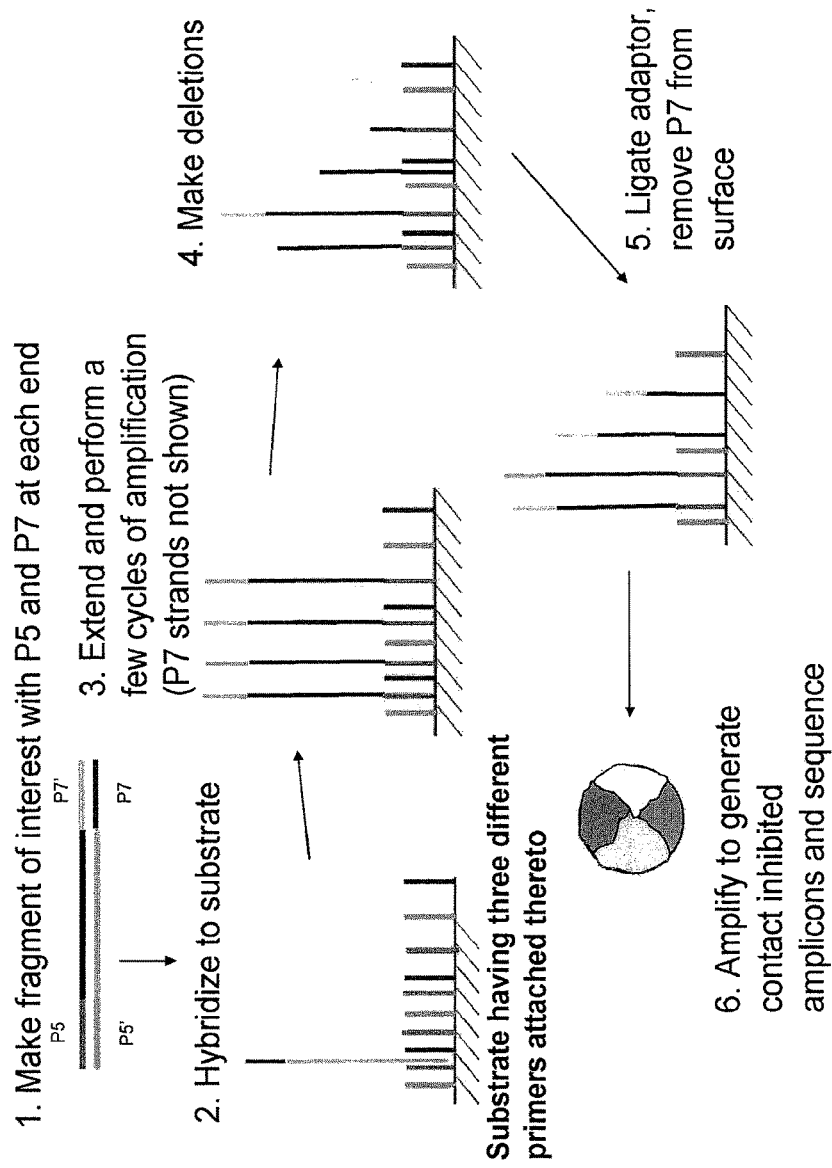
FIG. 3 is a schematic illustration showing a method of generating overlapping sequence reads and obtaining a contiguous nucleotide sequence of a nucleic acid of interest from deletion products having a different adaptor than attached to the full-length template.

As in FIG. 3, a duplex P5 adaptor is ligated to one end and a duplex P7 adaptor is ligated to the other end of a duplex target nucleic acid of interest and amplified. Amplified P5-target-P7 or P7-target-P5 duplexes are denatured to single-stranded templates and hybridized to array-attached capture probes complementary to the P5 and P7 adaptor sequence. Capture probes are fully extended with polymerase in the presence of natural nucleoside triphosphates and amplified by a few cycles of bridge amplification. Amplicons are then digested with exonuclease (e.g. exo III) or endonuclease (e.g. DNase I), yielding deletion products having lengths less than the full length of the templates. Digestion is stopped, templates are dehybridized, and single-stranded third adaptors (TA) are ligated with T4 ligase to the free ends of the deletion products. Capture probes complementary to P5 and/or P7 are removed or blocked on the array to prevent regeneration of full-length inserts during bridge amplification. P5-deletion product-TA or P7-deletion product-TA strands are bridge amplified on the array via TA-complementary capture probes attached to the array, and sequenced from the non-attached TA end by sequencing-by-synthesis to generate a set of overlapping sequencing reads. The overlapping sequencing reads are assembled to obtain a contiguous nucleotide sequence of the target nucleic acid.

Example 9

Figure 4:
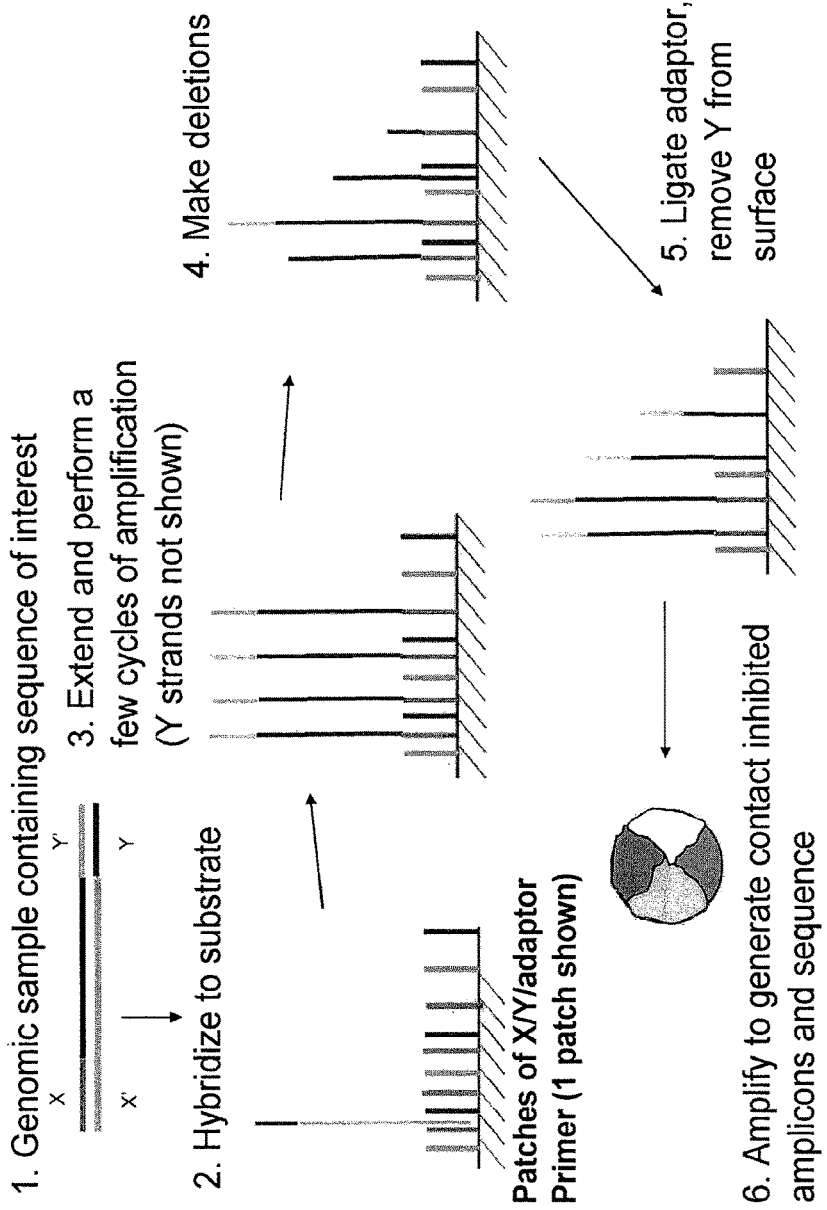
FIG. 4 is a schematic illustration showing a method of generating overlapping sequence reads and obtaining a contiguous nucleotide sequence of a nucleic acid fragment from deletion products having a different adaptor than attached to the full-length template.

As in FIG. 4, a genomic sample containing a sequence of interest is obtained. Different duplex genome specific adaptors (X and Y) are ligated to the ends of a duplex genomic sequence of interest, denatured to single-stranded templates, and hybridized to array-attached capture probes complementary to the genome specific adaptors (X and Y). The array attached capture probes are present at discrete locations such that a unique adaptor is recruited to a respective location based on probe-adaptor complementarity. In this way targeted capture is achieved. Capture probes are fully extended with polymerase in the presence of natural nucleoside triphosphates and amplified by a few cycles of bridge amplification. Amplicons are then digested with exonuclease (e.g. exo III) or endonuclease (e.g. DNase I), yielding deletion products having lengths less than the full length of the templates. Digestion is stopped, templates are dehybridized, and single-stranded third adaptors (TA) are ligated with T4 ligase to the free ends of the deletion products. Capture probes complementary to genome specific adaptors X and/or Y can be removed or blocked but is not necessary. X-deletion product-TA and Y-deletion product-TA strands are bridge amplified on the array via TA-complementary capture probes attached to the array, and sequenced from the non-attached TA end by sequencing-by-synthesis to generate a set of overlapping sequencing reads. The overlapping sequencing reads are assembled to obtain a contiguous nucleotide sequence of the target nucleic acid.

Example 10

A duplex P5 adaptor is ligated to one end of a duplex target nucleic acid of interest and amplified. Amplified P5-target duplexes are denatured to single-stranded templates and hybridized to array-attached capture probes complementary to the P5 adaptor sequence. Capture probes are extended with the Klenow fragment of pol I in the presence of d-isoGTP. Complements of the extended capture probes having incorporated isoG are synthesized using TiTaq polymerase in the presence of d-isoCTP.

A sequencing primer is hybridized to extended capture probes or their complements and extended in the presence of natural nucleotides until extension stalls at the point of incorporation of the first modified nucleotide isoG or isoC incorporated in the template. A complementary modified nucleotide isoG or isoC is incorporated at the point of stall using TiTaq polymerase and a sequencing read is initiated at the first base after the point of incorporating isoG or isoC by sequencing-by-synthesis to generate a set of overlapping sequencing reads corresponding to the various points of initiating sequencing reads. The overlapping sequencing reads are assembled to obtain a contiguous nucleotide sequence of the target nucleic acid.

Example 11

Figure 5:
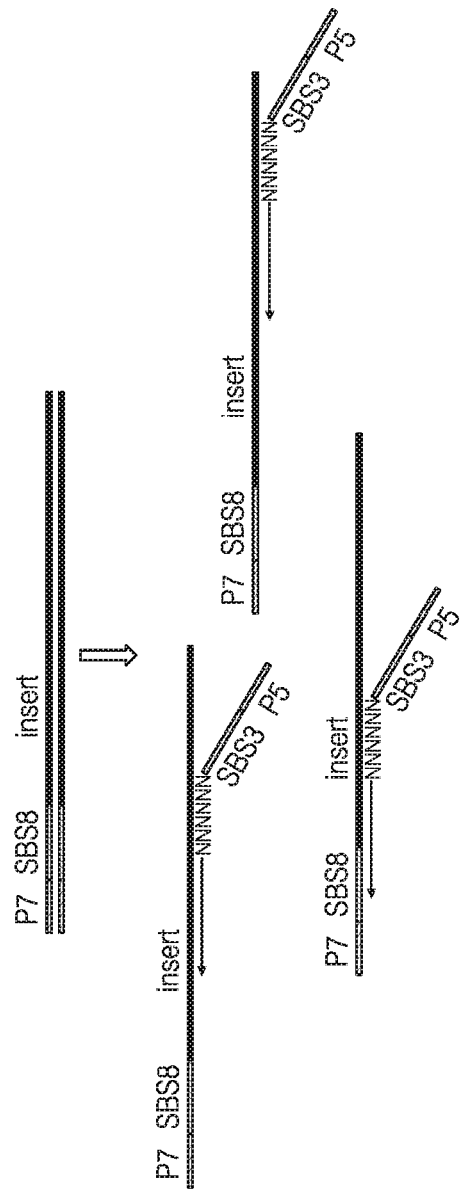
FIG. 5 is a schematic illustration showing a method of generating overlapping sequence reads and obtaining a contiguous nucleotide sequence of a nucleic acid of interest from deletion products formed by extending random primers that hybridize to the nucleic acid of interest.

As in FIG. 5, a duplex P7 adaptor and sequencing-by-synthesis oligonucleotide (SBS8) are ligated to one end of a duplex target nucleic acid of interest. The P7-SBS8-target duplex is denatured and hybridized with primers having a random hexamer oligonucleotide adjacent to an SBS3-P5 adaptor oligonucleotide (NNNNNN-SBS3-P5). Several rounds of extension with a polymerase generate single-stranded template deletion products of various overlapping lengths with respect to the full-length target nucleic acid of interest. The various single-stranded P7-SBS8-template-SBS3-P5 deletion products are hybridized to array-attached capture probes complementary to the P7 and P5 adaptor sequence. Capture probes are fully extended with polymerase in the presence of natural nucleoside triphosphates, amplified by a few cycles of bridge amplification, and sequenced from the non-attached end by sequencing-by-synthesis using SBS8 and/or SBS3 primers to generate a set of overlapping sequencing reads. The overlapping sequencing reads are assembled to obtain a contiguous nucleotide sequence of the target nucleic acid.

Example 12

Figure 6:
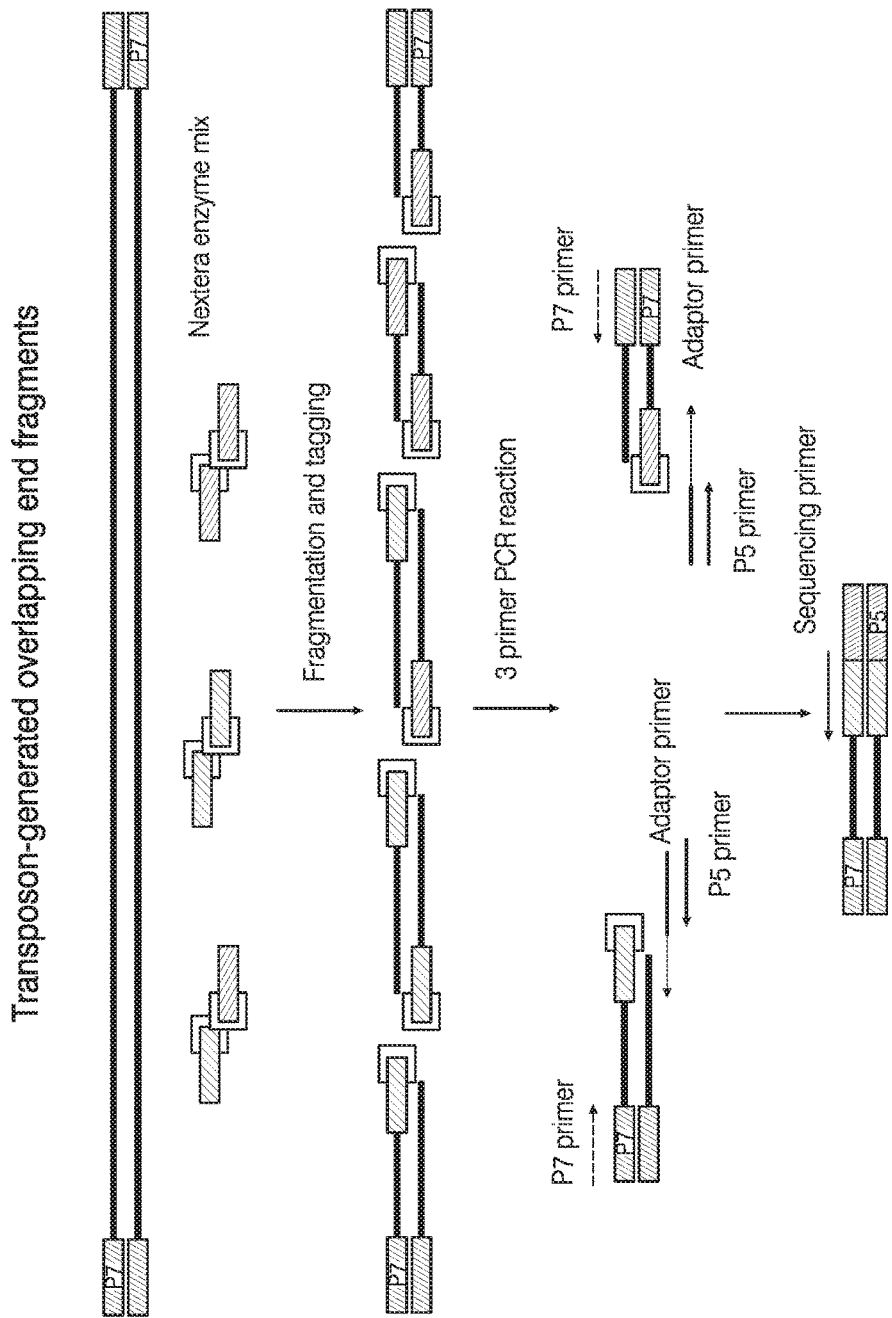
FIG. 6 is a schematic illustration showing a method of generating overlapping sequence reads and obtaining a contiguous nucleotide sequence of a nucleic acid of interest from deletion products formed by using transposons to generate overlapping end fragments of the nucleic acid of interest.

As in FIG. 6, transposase, transposon ends appended to a sequencing primer site 1 (SPS1), and transposon ends appended to a sequencing primer site 2 (SPS2) are incubated with duplex target nucleic acid having duplex P7 adaptors attached to both ends. Transposase promotes random insertion of transposon ends at various positions in the duplex nucleic acid of interest and random generation of duplex fragments covalently tagged with a transposon end appended with SPS1 or SPS2 at one 5' end for an end fragment, or at both 5' ends for an internal fragment. The fragments are then amplified in a 3 primer PCR reaction using a P7 primer, an adaptor primer which includes SPS1 or SPS2 appended to a P5 primer, and a P5 primer. The PCR reaction enriches for deletion products corresponding to varying lengths with respect to the ends of the target nucleic acid by generating duplex P7-target 5' end fragment-(SPS1 or SPS2)-P5 amplicons and P5-(SPS1 or SPS2)-target 3' end fragment-P7 amplicons. Subsequently, the amplicons are hybridized to array-attached capture probes complementary to the P7 and P5 adaptor sequence. Capture probes are fully extended with polymerase in the presence of natural nucleoside triphosphates, amplified by a few cycles of bridge amplification, and sequenced from the non-attached end by sequencing-by-synthesis using SPS1 or SPS2 primers to generate a set of overlapping sequencing reads. The overlapping sequencing reads are assembled to obtain a contiguous nucleotide sequence of the target nucleic acid.

Example 13

Figure 7:
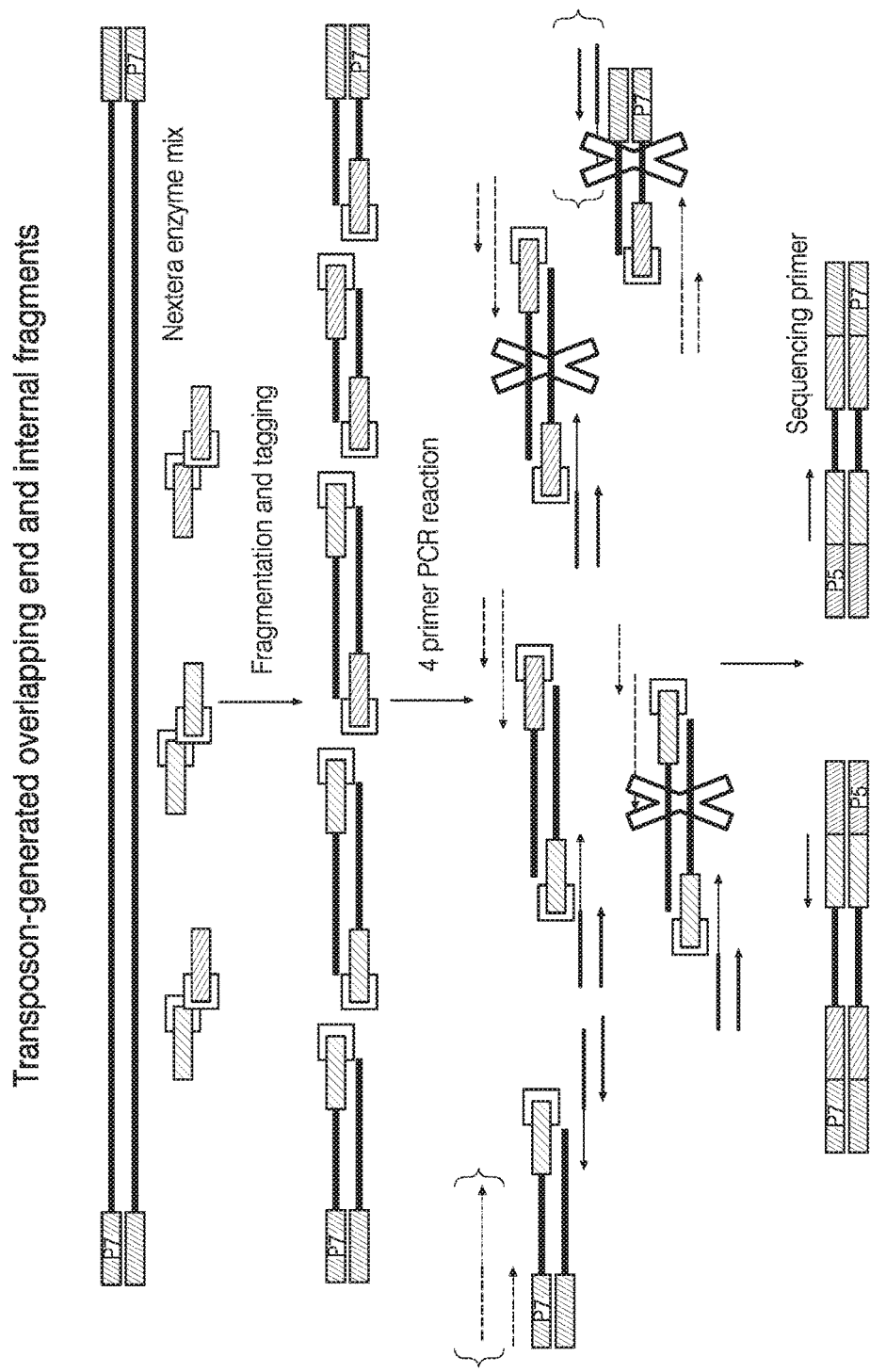
FIG. 7 is a schematic illustration showing a method of generating overlapping sequence reads and obtaining a contiguous nucleotide sequence of a nucleic acid of interest from deletion products formed by using transposons to generate both overlapping end fragments and internal fragments of the nucleic acid of interest.

As in FIG. 7, transposon-mediated fragmentation of duplex target nucleic acid is performed according to the method described in Example 12. In addition to amplifying end fragments of the target nucleic acid, internal fragments flanked by SPS1 on one end and SPS2 on the other end are also enriched by performing suppression PCR. The target nucleic acid fragments are amplified in a 4 primer suppression PCR reaction using a P7 primer, a P5 primer, an adaptor primer which includes SPS1 appended to a P5 primer and an adaptor primer which includes SPS2 appended to a P7 primer. Subsequently, the amplicons are hybridized to array-attached capture probes complementary to the P7 and P5 adaptor sequence. Capture probes are fully extended with polymerase in the presence of natural nucleoside triphosphates, amplified by a few cycles of bridge amplification, and sequenced from the non-attached end by sequencing-by-synthesis using SPS1 or SPS2 primers to generate a set of overlapping sequencing reads. The overlapping sequencing reads are assembled to obtain a contiguous nucleotide sequence of the target nucleic acid.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention.

All references cited herein including, but not limited to, published and unpublished applications, patents, and literature references, are incorporated herein by reference in their entirety and are hereby made a part of this specification. To the extent publications and patents or patent applications incorporated by reference contradict the disclosure contained in the specification, the specification is intended to supersede and/or take precedence over any such contradictory material.

What is claimed is:

1. A method of generating overlapping sequencing reads, said method comprising:
   providing a plurality of polynucleotides;
   processing said plurality of polynucleotides by extending random primers hybridized to a polynucleotide of said plurality of polynucleotides and/or randomly fragmenting a double-stranded polynucleotide of said plurality of polynucleotides using transposition, so as to produce a set of overlapping nucleotide regions to be sequenced;

providing a substrate having a surface, said surface comprising a site having said set of overlapping nucleotide regions attached thereto; and sequencing said set of overlapping nucleotide regions, thereby generating a set of overlapping sequencing reads.

2. The method of claim 1, further comprising the step of assembling sequencing reads from said set of overlapping sequencing reads so as to obtain a contiguous nucleotide sequence of a nucleic acid of interest.

3. The method of claim 2, wherein at least one of said polynucleotides comprises said contiguous nucleotide sequence of the nucleic acid of interest.

4. The method of claim 1, wherein said processing step generates an overlapping set of deletion products from said plurality of polynucleotides.

5. The method of claim 4, wherein said plurality of nucleotides are attached to said site before said processing step.

6. The method of claim 4, wherein said plurality of nucleotides are attached to said site after said processing step.

7. The method of claim 4, further comprising amplifying said set of deletion products on the surface to form amplicons corresponding to the set of deletion products.

8. The method of claim 1, wherein said random primers comprise a random nucleotide sequence suitable for random priming and initiation of polymerase-mediated extension.

9. The method of claim 8, wherein said random primers further comprise a sequencing primer site, an adaptor sequence, or a combination thereof.

10. The method of claim 1, wherein said transposition comprises a transposase enzyme fragmenting said double-stranded polynucleotide at random positions and attaching resulting fragments to oligonucleotide sequences comprising transposon ends.

11. The method of claim 10, wherein said oligonucleotide sequences further comprise a sequencing primer site, an adaptor sequence, or a combination thereof.

12. The method of claim 11, which generates deletion products corresponding to end fragments of said double-stranded polynucleotide flanked by one transposon end.

13. The method of claim 11, which generates deletion products corresponding to internal fragments of said double-stranded polynucleotide flanked by two transposon ends.

* * * * *

UNITED STATES PATENT AND TRADEMARK OFFICE
CERTIFICATE OF CORRECTION

PATENT NO. : 10,370,709 B2
APPLICATION NO. : 15/263203
DATED : August 6, 2019
INVENTOR(S) : Roberto Rigatti et al.

Page 1 of 1

It is certified that error appears in the above-identified patent and that said Letters Patent is hereby corrected as shown below:

On the Title Page

Column 1
Item "(71) Applicant:"
Delete "Ilumina" and insert -- Illumina --, therefor.

Signed and Sealed this
Twenty-sixth Day of May, 2020

Andrei Iancu
*Director of the United States Patent and Trademark Office*